(12) United States Patent
Dumesic et al.

(10) Patent No.: US 8,772,515 B2
(45) Date of Patent: Jul. 8, 2014

(54) METHOD TO CONVERT BIOMASS TO 5-(HYDROXYMETHYL)-FURFURAL (HMF) AND FURFURAL USING LACTONES, FURANS, AND PYRANS AS SOLVENTS

(71) Applicant: Wisconsin Alumni Research Foundation, Madison, WI (US)

(72) Inventors: James A. Dumesic, Verona, WI (US); Jean Marcel Ribeiro Gallo, Madison, WI (US); David Alonso, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/649,891

(22) Filed: Oct. 11, 2012

(65) Prior Publication Data

US 2014/0107355 A1 Apr. 17, 2014

(51) Int. Cl.
*C07D 307/48* (2006.01)
(52) U.S. Cl.
USPC .............................. 549/489; 549/429; 549/483
(58) Field of Classification Search
USPC .......................................... 549/429, 483, 489
See application file for complete search history.

(56) References Cited

U.S. PATENT DOCUMENTS

| | | | | |
|---|---|---|---|---|
| 7,572,925 | B2 * | 8/2009 | Dumesic et al. | 549/488 |
| 7,880,049 | B2 * | 2/2011 | Dumesic et al. | 585/733 |
| 8,389,749 | B2 * | 3/2013 | Dumesic et al. | 549/489 |
| 2011/0071306 | A1 | 3/2011 | Robinson | |
| 2011/0207923 | A1 | 8/2011 | Moliner-Marin et al. | |

OTHER PUBLICATIONS

Alamillo, R., et al., The selective hydrogenation of biomass-derived 5-hydroxymethylfurfural using heterogeneous catalysts. *Green Chemistry*, 2012. 14(5): p. 1413-1419.
Alonso, D.M., Bond, J. Q., and Dumesic, J.A., Catalytic conversion of biomass to biofuels, *Green Chemistry*, 2010, 12, 1493-1513.
Amarasekara, A.S. , Williams, L.D. and Ebede, C.C., Mechanism of the dehydration of $_D$-fructose to 5-hydroxymethylfurfural in dimethyl sulfoxide at 150° C: an NMR study, *Carbohydrate Research*, 2008, 343, 3021-3024.
Antal Jr., M.J., Mok, W.S.L. and Richards, G.N., Mechanism of formation of 5-(hydroxymethyl)-2-furaldehyde from $_D$-fructose and sucrose, *Carbohydrate Research*, 1990, 199, 91-109.
Binder, J.B. and Raines, R.T., Simple Chemical Transformation of Lignocellulosic biomass into Furans for Fuels and Chemicals, *Journal of the American Chemical Society*, 2009, 131, 1979-1985.
Bozell, J.J. and Petersen, G.R., Technology development for the production of biobased products from biorefinery carbohydrates— the U.S. Deparmtent of Energy's "Top 10" revisited, *Green Chemistry*, 2010, 12, 539-554.
Cass, O.W., Chemical Intermediates Fro Furfural, *Industrial & Engineering Chemistry*, 1948, 40, 216-219.
Chheda, J.N., Roman-Leshkov, Y. and Dumesic, J.A., Production of 5-hydroxymethylfurfural and furfural by dehydration of biomass-derived mono- and poly-saccharides, *Green Chemistry*, 2007, 9, 342-350.
Crisci, A.J., Tucker, M.H., Lee, M.Y., Jang, S.G., Dumesic, J.A. and Scott, S.L, Acid-Functionalized SBA-15-Type silica Catalysts for Carbohydrate Dehydration, *ACS Catalysis*, 2011, 1, 719-728.
Davis, S.E., Houk, L.R., Tamargo, E.C., Datye, A.K. and Davis, R.J., Oxidation of 5-hydroxymethylfurfural over supported Pt, Pd and Au Ctalysts, *Catalysis Today*, 2011, 160, 55-60.
Davis, S.E., Zope, B.N. and Davis, R.J., On the mechanism of selective oxidation of 5-hydroxymethylfurfural to 2,5-furandicarboxylic acid over supported Pt and Au catalysts, *Green Chemistry*, 2012, 14, 143-147.
Dutta, S., et al., Direct conversion of cellulose and lignocellulosic biomass into chemicals and biofuel with metal chloride catalysts. *Journal of Catalysis*, 2012. 288: p. 8-15.
Garcia-Suarez, E.J., Balu, A.M., Tristany, M., Garcia, A.B., Philippot, K. and Luque, R., Versatile dual hydrogenation-oxidation nanocatalysts fir the aqueous transformation of biomass-derived platform molecules, *Green Chemistry*, 2012, 14, 1434-1439.
Guan, J., Cao, Q.A., Guo, X.C. and Mu, X.D., The mechanism of glucose conversion to 5-hydroxymethylfurfural catalyzed by metal chlorides in ionic liquid: A theoretical study, *Comput. Theor. Chem.*, 2011, 963, 453-462.
Huang, R.L., Qi, W., Su, R.X. and He, Z.M., Integrating enzymatic and acid catalysis to convert lucose into 5-hdroxymethylfurfural, *Chem. Commun.*, 2010, 46, 1115-1117.
Manzer, L.E., Catalytic synthesis of α-methylene-γ-valerolactone: a biomass-derived acrylic monomer, *Appl. Catal. A-Gen*, 2004, 272, 249-256.
Moliner, M., Roman-Leshkov, Y. and Davis, M.E., Tin-containing zeolites are highly active catalysts for the isomerization of glucose in water, *P. Natl. Acad. Sci. USA*, 2010, 107, 6164-6168.
Moreau, C., Finiels, A. and Vanoye, L., Dehydration of fructose and sucrose into 5-hydroxymethylfurfural in the presence of 1-H-3-methyl imidazolium chloride acting both as a solvent and catalyst, *Journal of Molecular Catalysis A: Chemical*, 2006, 253, 165-169.

(Continued)

*Primary Examiner* — Golam M M Shameem
(74) *Attorney, Agent, or Firm* — Joseph T. Leone, Esq.; DeWitt Ross & Stevens S.C.

(57) ABSTRACT

Described is a process to produce hydroxymethyl furfural (HMF) from biomass-derived sugars. The process includes the steps of reacting a C5 and/or C6 sugar-containing reactant derived from biomass in a monophasic or biphasic reaction solution comprising water and a co-solvent. The co-solvent can be beta-, gamma-, and/or delta-lactones derived from biomass, tetrahydrofuran (THF) derived from biomass, and/ or methyltetrahydrofuran (MTHF) derived from biomass. The reaction takes place in the presence of an acid catalyst and a dehydration catalyst for a time and under conditions such that at least a portion of glucose or fructose present in the reactant is converted to HMF.

30 Claims, 18 Drawing Sheets

(56) References Cited

OTHER PUBLICATIONS

Nikolla, E., Roman-Leshkov, Y., Moliner, M. and Davis, M.E., "One-Pot" Synthesis of 5-(Hydroxymethyl)furfural from Carbohydrates using Tin-Beta Zeolite, *ACS Catalysis*, 2011, 1, 408-410.

Osmundsen, C.M., Holm, M.S., Dahl, S. and Taarning, E., Tin-containing silicates: structure-activity relations, *Proceedings of the Royal Society A-Mathematical physical & Engineering Sciences*, 2012, 468, 2000-2016.

Pagan-Torres, Y.J., Wang, T.F., Gallo, J.M.R., Shanks, B.H. and Dumesic, J.A., Production of 5-Hydroxymethylfurfural from Glucose Using a Combination of Lewis and Brønsted Acid Catalysts in Water in a Biphasic Rector with an Alkylphenol Solvent, *ACS Catalysis*, 2012, 2, 930-934.

Pilath, H.M, Nimlos, M.R., Mittal, A., Himmel, M.E. and Johnson, D.K., Glucose Reversion Reaction Kinetics, *J. Agr. Food Chem.*, 2010, 58, 6131-6140.

Roman-Leshkov, Y., Chheda, J.N. and Dumesic, J.A., Phase Modifiers Promote Efficient Production of Hydroxymethylfurfural from Fructose, *Science*, 2006, 312, 1933-1937.

Roman-Leshkov, Y., Barrett, C.J., Liu, Z.Y. and Dumesic, J.A., Production of dimethylfuran for liquid fuels from biomass-derived carbohydrates, *Nature*, 2007, 447, 982-U985.

Román-Leshkov, Y. and Dumesic, J., Solvent Effects on Fructose Dehydration to 5-Hydroxymethylfurfural in Biphasic Systems Saturated with Inorganic Salts, *Topics in Catalysis*, 2009, 52, 297-303.

Serrano-Ruiz, J.C., Luque, R. and Sepulveda-Escribano, A., Transformations of biomass-derived platform molecules: from high added-value chemicals to fuels via aqueous-phase processing, *Chem. Soc. Rev.*, 2011, 40, 5266-5281.

Shah, P., Ramaswamy, A.V., Lazar, K. and Ramaswamy, V., Direct hydrothermal synthesis of mesoporous Sn-SBA-15 materials under eak acidic conditions, *Microporous and Mesoporous Materials*, 2007, 100, 210-226.

Shimizu, K.-I, Uozumi, R. and Satsuma, A., Enhanced production of hydroxymethylfurfural from fructose with solid acid catalysts by simple water removal methods, *Catalysis Communications*, 2009, 10, 1849-1853.

Takagaki, A., Ohara, M., Nishimura, S. and Ebitani, K., A one-pot reaction for biorefinery: combination of solid acid and base catalysts for direct production of 5-hydroxymethylfurfural from saccharides, *Chem. Commun.*, 2009, 6276-6278.

Tucker, M.H., Selective Production of Value Added Chemicals From Fructose Using Heterogeneous Catalysis, in *Chemical & Biological Engineering*. 2011, University of Wisconsin-Madison: Madison.

Ugurchieva, T.M., Lozanova, A.V., Zlokazov, M.V. and Veselovsky, V.V., Synthesis of (±)-4-alkanolides from pent-4-enoic acid, *Russian Chemical Bulletin, International Edition*, , 2008, 57, 657-659.

Werpy, T.A. and Petersen, G., Top Value Added Chemicals from Biomass vol. 1—Results of Screening for Potential Candidates from Sugars and Synthesis Gas, , U.S. Department of Energy, 2004.

Wettstein, S.G., Alonso, D.M., Chong, Y. and Dumesic, J.A., Production of levulinic acid and gamma-valerolactone (GVL) from cellulose using GVL as a solvent in biphasic systems, *Energy & Environmental Science*, 2012, 5, 8199-8203.

Wyman, C.E., et al., Coordinated development of leading biomass pretreatment technologies, *Bioresource Technology*, 2005. 96(18): p. 1959-1966.

Yang, Y., Hu, C.W., and Abu-Omar, M.M., Conversion of carbohydrates and lignocellulosic biomass into 5-hydroxymethylfurfural using $AlCl_3$ center dot $6H(2)O$ catalyst in a biphasic solvent system, *Green Chemistry*, 2012. 14(2): p. 509-513.

Yong, G., Zhang, Y. and Ying, J.Y., Efficient Catalytic System for the Selective Production of 5-Hydroxymethylfurfural from glucose and Fructose, *Angewandte Chemie International Edition*, 2008, 47, 9345-9348.

Zakrzewska, M.E., Bogel-Lukasik, E. and Bogel-Lukasik, R., Ionic Liquid-Mediated Formation of 5-Hydroxymethylfurfural—A Promising Biomass-Derived Building Block, *Chem. Rev.*, 2011, 111, 397-417.

Zhang, Y., Hidajat, K. and Ray, A.K., Optimal design and operation of SMB bioreactor: production of high fructose syrup by isomerization of glucose, *Biochemical Engineering Journal*, 2004, 21, 111-121.

Zhao, H., Holladay, J.E., Brown, H. and Zhang, Z.C., Metal Chlorides in Ionic Liquid Solvents Convert Sugars to 5-Hydroxymehtylfurfural, *Science*, 2007, 316, 1597-1600.

Zhou, Y., Woo, L.K. and Angelici, R.J., Solid acid catalysis of tandem isomerization-lactonization of olefinic acids, *Applied Catalysis A: General*, 2007, 333, 238-244.

Zope, B.N., Davis, S.E. and Davis, R.J., Influence of Reaction Conditions o Diacid Formation During Au-Catalyzed Oxidation of Glycerol and Hydroxymethylfurfural, *Topics in Catalysis*, 2012, 55, 24-32.

Wang, Jianjian, et al., Direct Conversion of Carbohydrates to 5-Hydroxymethylfurfural Using Sn-Mont Catalyst, Green Chemistry, Sep. 1, 2012, pp. 2506-2512, 14, 9.

Bicker, M., et al., Dehydration of D-Fructose to Hydroxymethylfurfural in Sub- and Supercritical Fluids, The Journal of Supercritical Fluids, Dec. 1, 2005, pp. 118-126, 36, 2.

Kuster, BFM, 5-Hydroxymethylfurfural (HMF). A Review Focussing on its Manufacture, Starch/Starke, Jan. 1, 1990, pp. 314-321, 42, 8.

Gallo, JMR et al., Production and Upgrading of 5-Hydroxymethylfurfural Using Heterogeneous Catalysts and Biomass-Derived Solvents, Oct. 26, 2013, pp. 85-90, 15, 26.

* cited by examiner

Solvent: mixture of water and lactone or tetrahydropyran;
Brønsted Acid: Amberlyst 70 (Amb70)
Lewis Acid: Sn-SBA-15 ($Sn^{+4}$/Silica), $SnO_2$/Al-β or Sn-β

Advantages:
- Solvents can be obtained from biomass
- Low Toxicity
- No mixing problems
- No need of phase separation
- Solid catalysts can be easily removed from reaction

METHOD TO CONVERT BIOMASS TO 5-(HYDROXYMETHYL)-FURFURAL (HMF) AND FURFURAL USING LACTONES, FURANS, AND PYRANS AS SOLVENTS

FEDERAL FUNDING STATEMENT

This invention was made with government support under W911NF-09-2-0010 awarded by the ARMY/ARO and DE-FG02-84ER13183 awarded by the US Department of Energy. The government has certain rights in the invention.

BACKGROUND

The conversion of renewable biomass resources into chemicals and fuels traditionally obtained from petroleum is strategically important to improve the sustainability of the chemical industry. Lignocellulosic biomass is the non-edible portion of biomass, and extensive research has been carried out in its conversion into platform molecules. The platform molecule 5-hydroxymethylfurfural (HMF), produced from the Brønsted acid-catalyzed dehydration of $C_6$ sugars (hexoses), is considered to be one of the top value-added chemicals.[1, 2] Mechanistic studies have shown that HMF is formed from the dehydration of the hexoses in the furanose form (5 member ring).[2-4] Although glucose is the most abundant and least expensive hexose, it presents low amounts of furanose isomer in solution (1% in water [5]), and its dehydration into HMF thus takes place with low selectivity. [6] In contrast, fructose, which presents 21.5% of the furanose form in aqueous solution,[5] can be dehydrated to HMF in higher yields using monophasic or biphasic solvent systems, and using homogeneous and heterogeneous BrIInsted acids.[7-13] Dumesic and co-workers[14, 15] employed a biphasic system consisting of an aqueous layer saturated with NaCl and containing fructose and HCl or $H_2SO_4$ as catalysts, in combination with an extracting organic layer to protect HMF from degradation reactions. Several alcohols, ketones and ethers were used as extracting organic layers, and yields for HMF as high as 70% were observed.[14, 15] In monophasic solvent systems using dimethyl sulfoxide or ionic liquids as solvents, HMF can be obtained with yields higher than 90%.[7, 11, 16] However, the separation and purification of HMF from these solvents are complicated.

While glucose can be obtained from cellulose by hydrolysis with yields of 98-100%, isomerization of glucose to fructose is economically limited to 42%,[17] requiring additional and expensive separation steps. As a consequence, the final market price of fructose is significantly higher than that of glucose. In order to obtain HMF in high yields from glucose, recent studies have aimed to use one-pot isomerization reactions to produce fructose by using a Lewis acid or Lewis base, followed by Brønsted acid-catalyzed dehydration of fructose to HMF. See Reaction Scheme 1 and FIG. 1. Reaction Scheme 1 depicts the conversion of glucose to HMF by a combined isomerization/dehydration reaction pathway. FIG. 1 is a very abbreviated reaction scheme showing how furfural and HMF can be derived from a biomass feedstock.

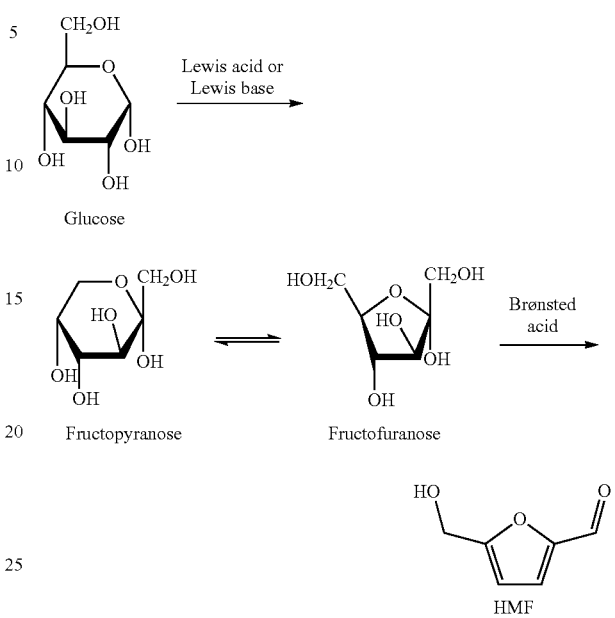

Reaction Scheme 1

Zhao et al.[18] first reported HMF yields of 68-70% from glucose in the ionic liquid 1-ethyl-3-methyl-imidazolium chloride using $CrCl_2$ as the Lewis acid catalyst. In subsequent studies with ionic liquids, HMF was produced from glucose with yields higher than 90%.[19] However, ionic liquids are not suitable for large scale applications due to their high cost and deactivation by small amounts of water.[7] Binder, et al.[12] reported that a system using dimethylacetamide (DMA), NaBr and $CrCl_2$ resulted in HMF yields of 81%, being as effective as ionic liquid systems. Other authors have explored biphasic systems. Huang et al.[20] reported a 63% HMF yield in a biphasic reactor system with a two-step process involving the isomerization of glucose to fructose in the presence of glucose isomerase and borate ions, followed by the HCl-catalyzed dehydration of fructose to HMF. Dumesic and co-workers [6] reported 62% yield of HMF from glucose using a biphasic reactor consisting of $AlCl_3 \cdot 6H_2O$ and HCl as catalysts in water saturated with NaCl, in contact with sec-butylphenol Abu-Omar et al. reported an HMF yield of 61% from glucose using $AlCl_3 \cdot 6H_2O$ as the catalyst in a biphasic system where THF was used as the extracting solvent [43, 44]. In all of these systems, the main goal was to maximize HMF yield, while the upgrading and purification of HMF and the sustainability of the process remained as secondary problems. For example, reutilization of homogeneous catalysts can be an issue, and these catalysts lead to corrosions problems that require expensive materials of construction. Moreover, the replacement of these homogeneous catalysts with heterogeneous catalysts is not possible in the presence of salts, due to exchange of protons on the catalyst with cations in solution, leading to deactivation of the heterogeneous catalyst.

Recent studies have shown that hydrotalcites [28] and tin containing zeolites and silicas [29] are active for glucose isomerization to fructose. Using a combination of Sn-β and HCl in a biphasic system, Nikolla et al. [30] obtained HMF yields of 57% at 79% conversion of glucose. No tin leaching was observed. Takagaki, et al. [28] reported HMF yields of 42% at 73% conversion in a two-step process by combining the solid Brønsted acid catalyst, Amberlyst-70 (Amb-70), and a solid base catalyst, hydrotalcite, in N,N-dimethylformamide.

HMF is an important chemical intermediate for a host of downstream reactions. The main reaction pathways for the production of chemicals from HMF are oxidation and hydrogenation. See FIG. 2 for a summary of exemplary reactions that can be conducted using furfural or HMF as the starting material. Hydrogenation, for example, can lead to 2,5-dihydroxymethylfuran (DHMF) or 2,5-dihydroxymethyltetrahydrofuran (DHMTHF) (not shown in FIG. 2). Both compounds are important solvents and monomers for commercially produced polymers [41]. Additionally there has been much commercial interest in converting HMF to 2,5-furandicarboxylic acid (FDCA). FDCA can be used as a monomer or co-monomer to make fiber and packaging polyesters that compete with polyethylene terephthalate (PET). PET is a commodity polymer that ranks third in world-wide production volume, trailing only polyethylene and polypropylene. World-wide PET production was 49 million tons in 2009.[37]

The focus of the research to date on HMF production has been on optimizing yields via the judicious selection of solvents and catalysts. But there has been very little research on the feasibility and economics of separating the HMF product from the solvent and catalysts used in the production process. Similarly, there has been very little research on how to integrate the glucose-to-HMF dehydration reaction to downstream reactions to upgrade the HMF into value-added chemicals. In the literature examples mentioned above, intricate separation steps are required to recover the catalysts. Economically speaking, the catalysts are sufficiently expensive that they must be recovered to make the processes financially viable. Even if heterogeneous catalysts are used (thus rendering recovery very simple), separating HMF from a high boiling point solvent quickly and economically is not so straightforward. Distillation at high temperatures risks polymerization of the HMF; vacuum distillation increases the cost of the purification.

One of the main drawbacks of the biphasic systems reported by date are that they rely on using salts to drive separation of the two phases and to increase the partition of the HMF into the organic phase. The use of salts in the aqueous phase complicates the use of solid catalysts because they are not long-lasting in the aqueous phase (leaching, collapse) and the acid sites are exchanged by the cation present in the salt, leading to the formation of homogeneous mineral acids. These mineral acids need to be removed from the HMF before further upgrading reactions can be conducted.

Thus, for the economic viability and environmental sustainability of the HMF production process there is a long-felt and unmet need to use of heterogeneous catalysts that can be easily removed from the reaction and a stable solvent that can be easily separated from the HMF product and recycled. If the solvent itself can be obtained from biomass, it too is sourced from renewable resources.

Furfural is another interesting building block which can be obtained from biomass. Furfural is typically produced by the dehydration of C5 sugars (e.g., xylose or arabinose) in the presence of an acid catalyst. Furfural can be converted into value-added chemicals such as furfuryl alcohol, tetrahydrofuran, furan, levulinic acid, and gamma valerolactone (some of which can be used as solvents for the process described herein).

SUMMARY OF THE INVENTION

Disclosed is a process to produce 5-hydroxymethylfurfural (HMF) and furfural from biomass. The process comprises reacting biomass, cellulose, or any other C6 sugar-containing reactant in a monophasic or biphasic reaction solution comprising an organic solvent, which can be biomass derived beta-, gamma- and delta-lactones, hydrofurans and hydropyrans; water can be used as a co-solvent. The reaction is conducted in the presence of an acid catalyst for a time and under conditions such that at least a portion of the C6 sugars present in the reactant is converted to HMF.

The process may optionally further comprise adding a saturating amount of salt to the reaction solution, wherein a biphasic reaction solution is formed.

In certain version of the process, the reaction solution is monophasic and comprises the organic solvent and, if desired, water. The organic solvent is selected from the group consisting of water-miscible hydrofurans, hydropyrans, beta-, gamma- and delta-lactones, and hydrofurans, and hydropyrans. Gamma-lactones and tetrahydrofuran containing 10 wt % water are preferred.

The acid catalyst may be a Brønsted acid, a Lewis acid or a combination of Brønsted and Lewis acids. The acid catalyst may be homogeneous or a solid acid catalyst.

The method may further comprise hydrogenating the HMF in the presence of a hydrogenation catalyst to yield dimethylfuran.

Similarly, the method may further comprise oxygenating the HMF in the presence of an oxygenation catalyst to yield furandicarboxylic acid and other oxidation products, such as 5-hydroxymethylfuranoic acid (HFCA) by oxidation of the formyl group, or 2,5-diformylfuran (DFF) by oxidation of the hydroxy group.

Another permutation of the method comprises reacting the biomass, cellulose or any other C6 sugar-containing reactant derived from biomass in a monophasic reaction solution, followed by creating a biphasic system having an aqueous phase and an organic phase by adding water and hydrocarbon to the monophasic reaction solution, whereby at least a portion of the HMF is extracted into the resulting aqueous phase. The method may further comprise hydrogenating the HMF in the presence of a hydrogenation catalyst to yield dimethylfuran. Alternatively, the method may further comprise oxygenating the HMF in the presence of an oxygenation catalyst to yield furandicarboxylic acid.

More specifically, disclosed and claimed herein is a process to produce 5-hydroxymethylfurfural (HMF). The process comprises reacting a C6 sugar-containing reactant in a monophasic reaction solution comprising (i) an organic solvent selected from the group consisting of beta-, gamma-, and delta-lactones, hydrofurans, hydropyrans, and combinations thereof, and (ii) at least about 1 wt % water; in the presence of a heterogeneous acid catalyst for a time and under conditions wherein at least a portion of the substrate present in the reactant is converted to HMF.

The organic solvent may be miscible with water, or the organic solvent may be immiscible with water, but capable of dissolving from 2 wt % to 25 wt % water. The organic solvent may be a combination of two or more solvents, wherein at least one of the solvents is miscible with water and at least one of the other solvents is not miscible with water, wherein the resulting mixture is either miscible with water or capable of dissolving from about 1% water to about 25 wt % water.

The HMF so formed may optionally be subjected to a hydrogenolysis reaction in the presence of a suitable catalyst, for a time and under conditions wherein at least a portion of the HMF is converted to dimethylfuran. Additionally, the HMF so formed may be oxygenated in the presence of an oxygenation catalyst, for a time and under conditions wherein at least a portion of the HMF is converted to furandicarboxylic acid.

The heterogeneous acid catalyst may be a solid acid catalyst selected from the group consisting of solid Brønsted acid catalysts, solid Lewis acid catalysts, and combinations thereof. For example, the solid acid catalyst may be a heteropolyacid, a mesoporous silica, a zeolite, an acidic material on a thermo-stable support (in which case the thermostable support may be selected from tin oxide, alumina, niobia, zirconia, titania, and carbon, among many other suitable selections), a solid acidic metal oxide, and/or a solid acidic ion exchanger. If a solid ion exchanger is used as the heterogeneous acid catalyst, it is preferred that it comprise crosslinked polystyrene-containing sulfonic acid groups and/or sulfonated tetrafluoroethylene-based fluoropolymer-copolymers.

When the heterogeneous acid catalyst is a solid Brønsted acid catalyst, a solid Lewis acid catalyst, or a combination of the two, the process may again optionally include subjecting the HMF to a hydrogenolysis reaction in the presence of a suitable catalyst for a time and under conditions wherein at least a portion of the HMF is converted to dimethylfuran. When the heterogeneous acid catalyst is a solid Brønsted acid catalyst, a solid Lewis acid catalyst, or a combination of the two, the process may again optionally include oxygenating the HMF in the presence of an oxygenation catalyst, for a time and under conditions wherein at least a portion of the HMF is converted to furandicarboxylic acid.

In any and all of the monophasic processes recited above, the monophasic reaction solution may comprise from about 5 wt % to about 25 wt % water, or from about 5 wt % to about 12 wt % water.

The process may further comprise, after reacting the C6 sugar-containing reactant to yield HMF, adding a sufficient quantity of a mixture of water and hydrocarbon to the monophasic reaction solution to create a biphasic system having an organic phase and an aqueous phase, wherein at least a portion of the HMF is extracted into the resulting aqueous phase. Once extracted into the aqueous phase, at least a portion of the HMF may optionally be subjected to a hydrogenolysis reaction in the presence of a suitable catalyst for a time and under conditions wherein at least a portion of the HMF is converted to dimethylfuran. Or, once extracted into the aqueous phase, at least a portion of the HMF may optionally be oxygenated in the presence of an oxygenation catalyst, for a time and under conditions wherein at least a portion of the HMF is converted to furandicarboxylic acid.

Another version of the process is directed to a process to produce 5-hydroxymethylfurfural (HMF). Here, the process comprises reacting a C6 sugar-containing reactant in a biphasic reaction solution comprising (i) an aqueous phase, and (ii) an organic phase comprising a water-immiscible solvent selected from the group consisting of beta-, gamma-, and delta-lactones, hydrofurans, hydropyrans, and combinations thereof; in the presence of an acid catalyst for a time and under conditions wherein at least a portion of the C6 sugar present in the reactant is converted to HMF. The aqueous phase may optionally comprise a saturating amount of a salt.

As noted for the other versions of the process, wherein the acid catalyst may be selected from the group consisting of Brønsted acid catalysts, Lewis acid catalysts, and combinations thereof. The catalyst may be homogeneous or heterogeneous. The organic solvent may have from four (4) carbon atoms to sixteen (16) carbon atoms, or from four (4) carbon atoms to eleven (11) carbon atoms. As noted in prior versions of the process, the process may further comprise oxygenating at least a portion of the HMF in the presence of an oxygenation catalyst, for a time and under conditions wherein at least a portion of the HMF is converted to furandicarboxylic acid. Additionally, the process may optionally comprise subjecting the HMF to a hydrogenolysis reaction in the presence of a suitable catalyst for a time and under conditions wherein at least a portion of the HMF is converted to dimethylfuran.

While glucose is obtained from cellulose in quantitative yield (98-100%), glucose isomerization to fructose is economically limited to roughly 42% [17]. As a consequence, the market price of fructose is often twice as high as the market price of glucose. Thus, the production of HMF from glucose instead of fructose is a more cost-effect process. Herein is disclosed and claimed an integrated process using solid acid catalysts and biomass-derived solvents, γ-lactones, hydrofurans and hydropyrans for converting glucose to HMF. Optionally, the HMF so formed may be upgrading by hydrogenation or oxidation. As depicted in Reaction Scheme 2, below, γ-valerolactone (GVL) can be obtained from hydrogenation of levulinic acid, another platform molecule derived from monosaccharide dehydration. In addition, GVL is an important platform molecule used for the production of chemicals and fuels.[21, 22] Other γ-lactones with higher molecular weights can be obtained from GVL, as described elsewhere,[23, 24] or by ring closing of unsaturated acid.[25] Thus, in addition to using GVL, the Examples below also disclose reactions using γ-hexylactone (GHL), γ-octalactone (GOL) and γ-undecalactone (GUL). Similar to GVL, THF can be derived from biomass from the decarbonylation and hydrogenation of furfural, a product of xylose dehydration. [26, 27]

Reaction Scheme 2

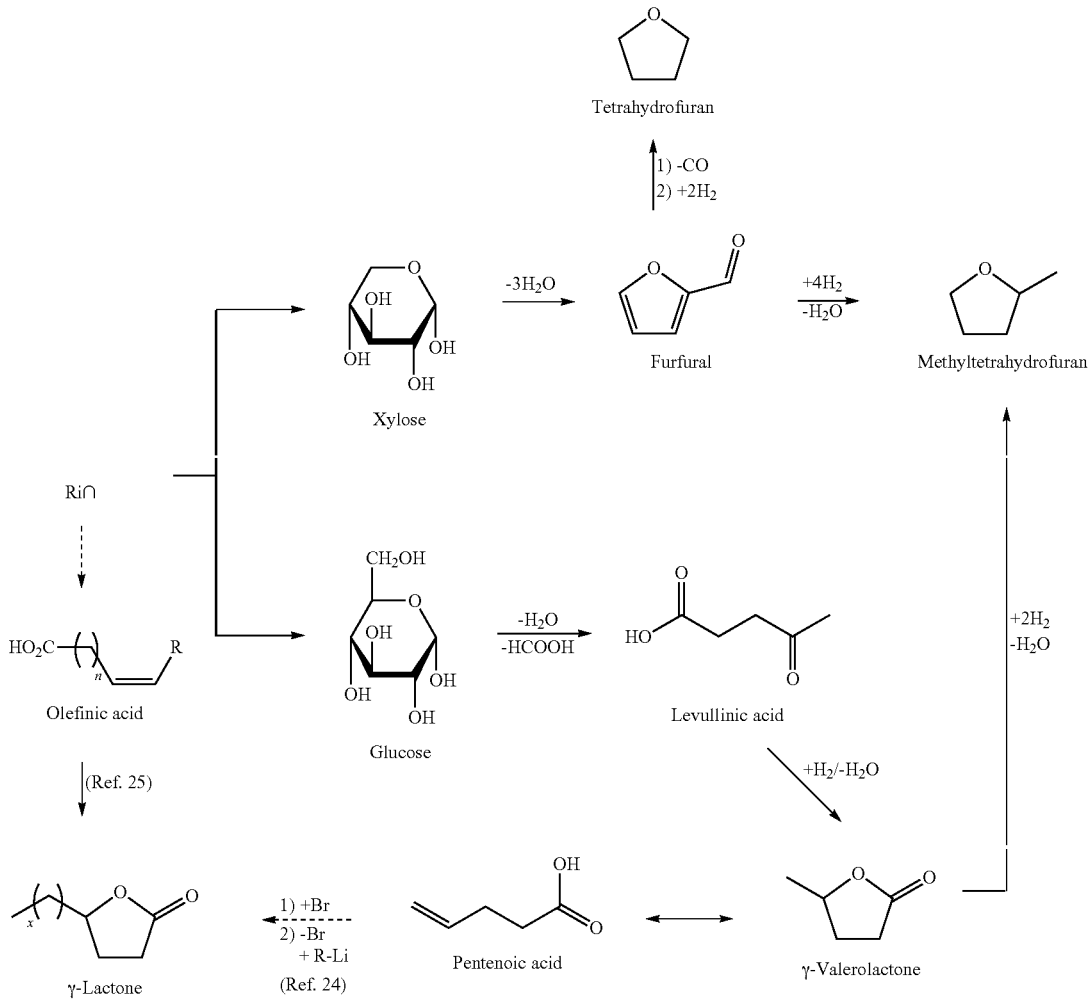

As described in greater detail below, the sustainability of the biomass conversion process would be improved by the use of biomass-derived solvents, alleviating the need to purchase and transport petroleum-derived solvents to the biomass conversion site. These solvents must operate in the presence of solid catalysts at reaction conditions favorable for glucose and/or fructose dehydration, and optimally they should be compatible with upgrading processes, which typically involve oxidation, hydrogenation, and/or hydrogenolysis reactions (although this is not required).

Thus, in the present method, lactones, hydrofurans and hydropyrans are used to produce HMF and furfural from biomass-derived starch, cellulose, glucose and/or fructose using homogeneous or heterogeneous catalysts. Also disclosed herein are methodologies to separate HMF from the reaction medium and to upgrade the HMF to FCDA, in an integrated process that can start from starch, cellulose, glucose or fructose yielding HMF, FCDA, or other value-added chemicals as the final products.

BRIEF DESCRIPTION OF THE DRAWINGS

FIG. 15A depicts glucose dehydration in GVL. FIG. 15B depicts glucose dehydration in GHL. FIG. 15C depicts glucose dehydration in THF. FIG. 15D depicts glucose dehydration in MTHF. FIG. 15E depicts glucose dehydration in THF:MTHF (1:1). All solvents contained 10% water. For all reactions: 2 wt % glucose; 0.05 g Sn-β; 0.05 g Amb-70; T=130° C.

DETAILED DESCRIPTION

Figure 1:
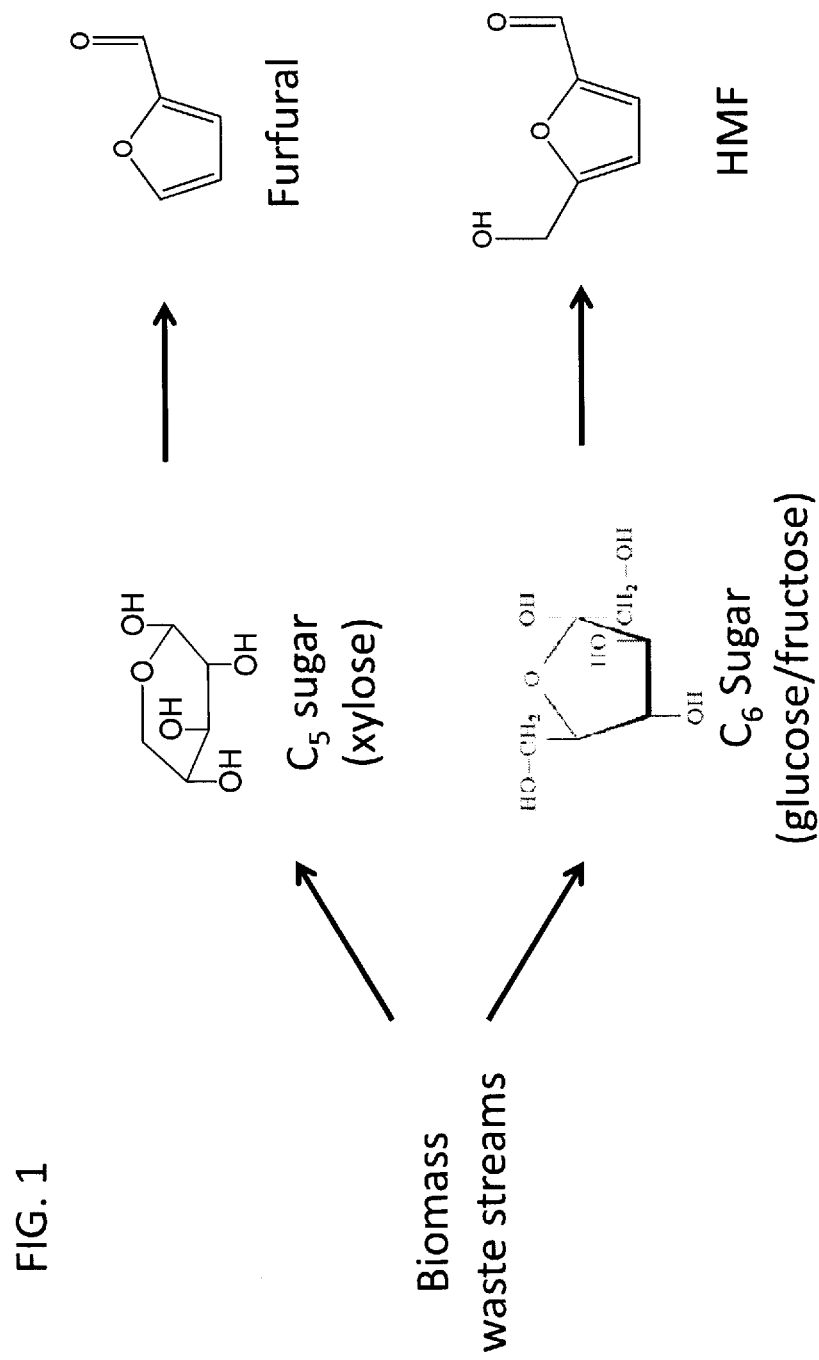
FIG. 1 is a reaction scheme depicting conversion of C5 sugars from biomass into furfural and conversion of C6 sugars from biomass into hydroxymethylfurfural (HMF).
Figure 2:
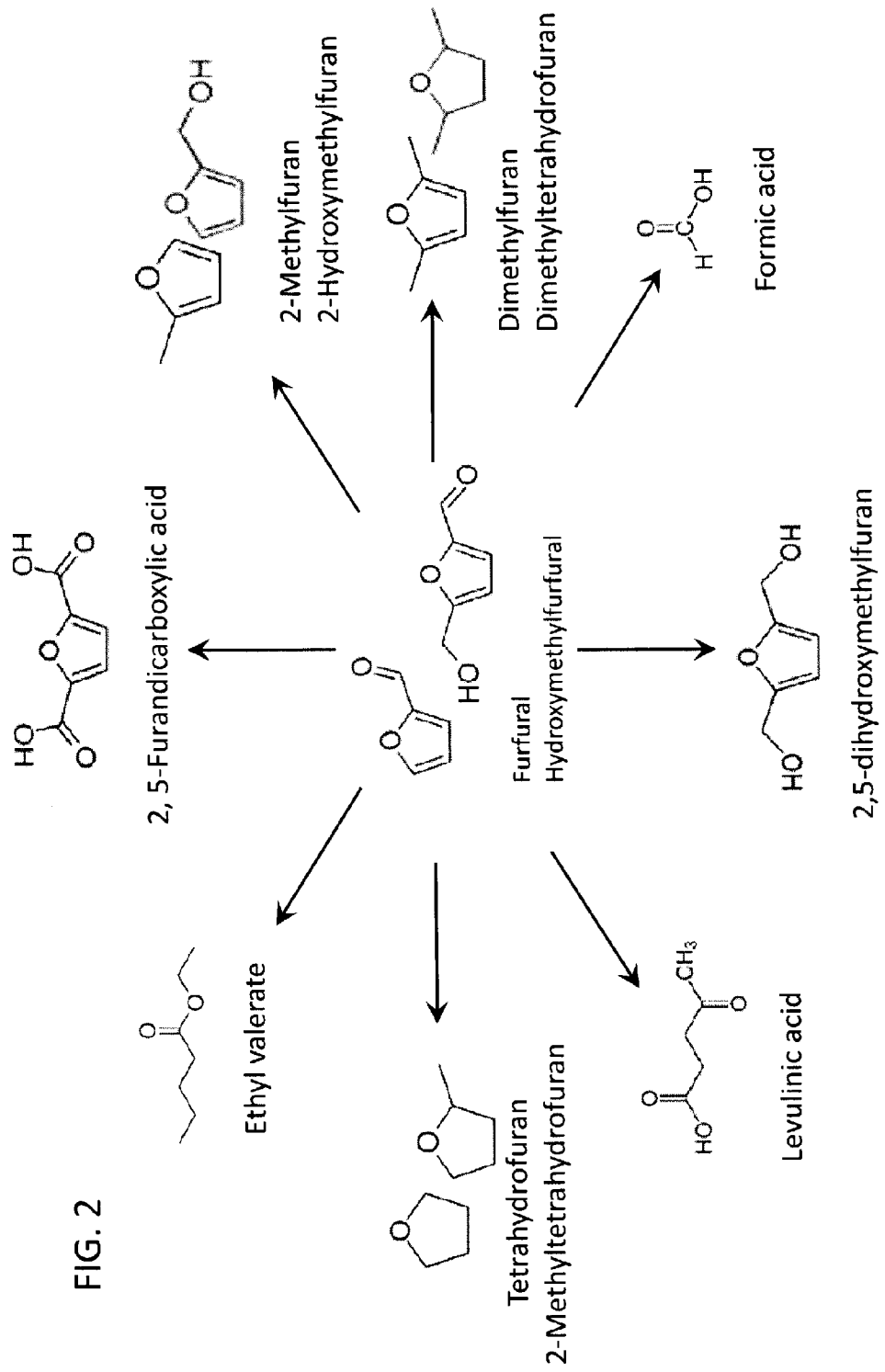
FIG. 2 is a reaction scheme depicting various downstream, value-added chemicals that can be made from furfural and/or HMF.

Abbreviations and Definitions:

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass. Glucose for use in the disclosed method may be biomass-derived.

Brønsted-Lowry Acid/Base=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers ($(C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose. For the experiments described below, microcrystalline cellulose (5% moisture, average size 20 μm) was obtained from Sigma-Aldrich, St. Louis, Mo. Dried corn stover was obtained through the Great Lakes Bioenergy Research Center, Madison, Wis., USA.

"Dehydration catalyst" means any catalyst, without limitation, whether now known or developed in the future, capable of removing water from organic compounds.

"Glucose-containing oligomers, glucose-containing polymers, Glucose-containing reactant, C6-containing reactant"=Any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12WO$_6$ octahedra. The standard unit has a net ($^-$3) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B,* 102:10817-10825.

"Homogeneous catalyst"=A catalyst that exists in the same phase (solid, liquid, or gas) as the reactants under reaction conditions. "Heterogeneous catalyst"=A catalyst that exists in a different phase than the reactants under reaction conditions.

"Hydrofuran" is used herein to refer to any unsubstituted or substituted cyclic ester having a single oxygen heteroatom in the ring, and having five total atoms in the ring and which is derived from furanic compounds. Hydrofurans that are miscible in water, such as tetrahydrofuran (THF), are more appropriate for use in the monophasic reactions described herein. In the biphasic reactions, any hydrofuran may be used.

"Hydropyran" is used herein to refer to any unsubstituted or substituted cyclic ester having a single oxygen heteroatom in the ring, and having six total atoms in the ring and which is derived from pyranic compounds. Hydropyrans miscible in water are more appropriate for use in the monophasic reactions described herein. In the biphasic reactions, any hydropyran may be used.

As used herein, the term "hydrogenation catalyst" refers without limitation to any catalyst, now known or developed in the future, homogenous or heterogeneous, that catalyzes the hydrogenation of carbonyl bonds (C=O) and hydrogenolysis of alcohols (C—OH). Preferred catalysts will reduce carbonyl bonds and hydrogenolysis of alcohols preferentially versus carbon-carbon double bonds (C=C). The activities need not be exclusive, but the chosen catalyst should catalyze the hydrogenation of C=O bonds and hydrogenolysis of alcohols at a rate much larger than the catalyst catalyzes the hydrogenation of C=C bonds. Catalysts comprising one or more metals from Groups 6-14 are preferred, also these metals doped with gallium, boron, germanium, indium and/or tin. Ruthenium, nickel, platinum copper, chromium and rhodium (alone, in combination, alloyed with other metals, and/or doped with gallium, germanium, indium and/or tin) are preferred. Other hydrogenation catalysts may also be used, such as metal hydrides (e.g., NaBH$_4$), polyoxometalates, Raney Ni, Raney Cu, etc. The catalysts may be used with or without a support.

Selective reduction may also be accomplished by transfer hydrogenation using a hydrogen donor. The term "hydrogen donor" refers to any compound with the ability to transfer a hydrogen atom to other substance. Exemplary hydrogen donors which can be utilized include, but are not limited to primary and secondary alcohols, polyols, olefins, cycloalkenes, carboxylic acids, and esters.

The rate of H-transfer can be increased by using homogeneous or heterogeneous catalysts. Exemplary catalysts include, but are not limited to, metals, zeolites, metal oxides supported or unsupported such as MgO, ZrO$_2$, gamma-Al$_2$O$_3$, CeO$_2$, CeZrO$_x$, MgOAl$_2$O$_3$, Mg/Al/ZrO$_x$, MgO/SiO$_2$, CeO$_2$ZnO, Sn-beta-zeolite, Ti-beta-zeolite, Sn-containing mesoporous silica, as well as metal salts and complexes of Pd, Pt, Ru, Ir, Rh, Fe, Ni, Co, Os, Mo. A full list of suitable hydrogen donors and catalysts can be found in R.A.W Johnsotne & A.H Wilby (1985) "Heterogeneous catalytic transfer hydrogenation and its relation to other methods for reduction of organic compounds," *Chem. Rev.* 85: 129-170, which is incorporated herein by reference.

"Lactone" as used herein refers to an unsubstituted or substituted cyclic ester, having a single oxygen heteroatom in the ring, and having from four to six total atoms in the ring—i.e., beta, gamma, and delta lactones, derived from any corresponding C$_4$ to C$_{16}$ carboxylic acid. Thus, as used herein, the term "lactone" explicitly includes (without limitation) unsubstituted and substituted beta and gamma-butyrolactone and beta-, gamma-, and delta-valerolactones to beta-, gamma, and delta-hexadecalactones. Some lactones are miscible in water, such as GVL; other lactones have more limited solubility in water. Those lactones that can dissolve at least about 1 wt % water, and more preferably at least about 5 wt % (or more) of water (up to miscible) are suitable for use in the monophasic reactions described herein. In the other hand, any lactone is suitable to biphasic system.

As used herein, the term "oxygenation catalyst" refers without limitation to any catalyst, now known or developed in the future, homogenous or heterogeneous, that catalyzes the oxygenation of alcohols and/or aldehydes. The oxidation reaction may be partial or complete (i.e., oxidation from alcohol to aldehyde or ketone; or oxidation from alcohol to carboxylic acid). Oxidation catalysts may comprise, but are not limited to, alkaline earth metals, rare earth metals, chromium, manganese, molybdenum, tungsten, tin, rhenium, bismuth, indium, phosphorus, iron, cobalt, nickel, ruthenium, rhodium, palladium, osmium, iridium, platinum, oxides thereof, derivatives thereof, mixtures thereof, or combinations thereof.

The hydrogenation and/or oxygenation catalysts may be disposed on a catalyst support material, such as a refractory oxide. For example, the refractory oxide can be alumina, particularly alpha alumina, zirconia, titania, hafnia, silica; or mixtures thereof. The catalyst support material can be or can include rare earth-modified refractory metal oxides, where the rare earth may be any rare earth metal, for example, lanthanum or yttrium; and/or alkali earth metal-modified refractory oxides. The catalyst support material can be categorized as materials having a substantially stable surface area at reaction conditions, for example, a surface area that is not substantially altered by reaction conditions or altered in a way that affects the reaction.

FA=formic acid. FDCA=2,5-furandicarboxylic acid. FID=flame ionization detector. GHL=gamma-heaxlactone. GOL=gamma-octolactone. GUL=gamma-undecalactone. GVL=gamma-valerolactone (γ-valerolactone). HMF=5-hydroxymethylfurfural. HPLC=high-performance liquid chromatography. LA=levulinic acid. SA=sulfuric acid. Mineral acid=any mineral-containing acid, including (by way of example and not limitation), hydrochloric acid, nitric acid, phosphoric acid, SA, boric acid, hydrofluoric acid, hydrobromic acid, and the like. Organic acid=any organic acid, without limitation, such as toluenesulfonic acid, formic acid, acetic acid, trifluoroacetic acid, oxalic acid, and the like. PET=polyethylene terephthalate. CP=cyclopentane. MCP=methylcyclopentane. THF=Tetrahydrofuran. MTHF=2-methyltetrahyddrofuran Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$.and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

Figure 3:
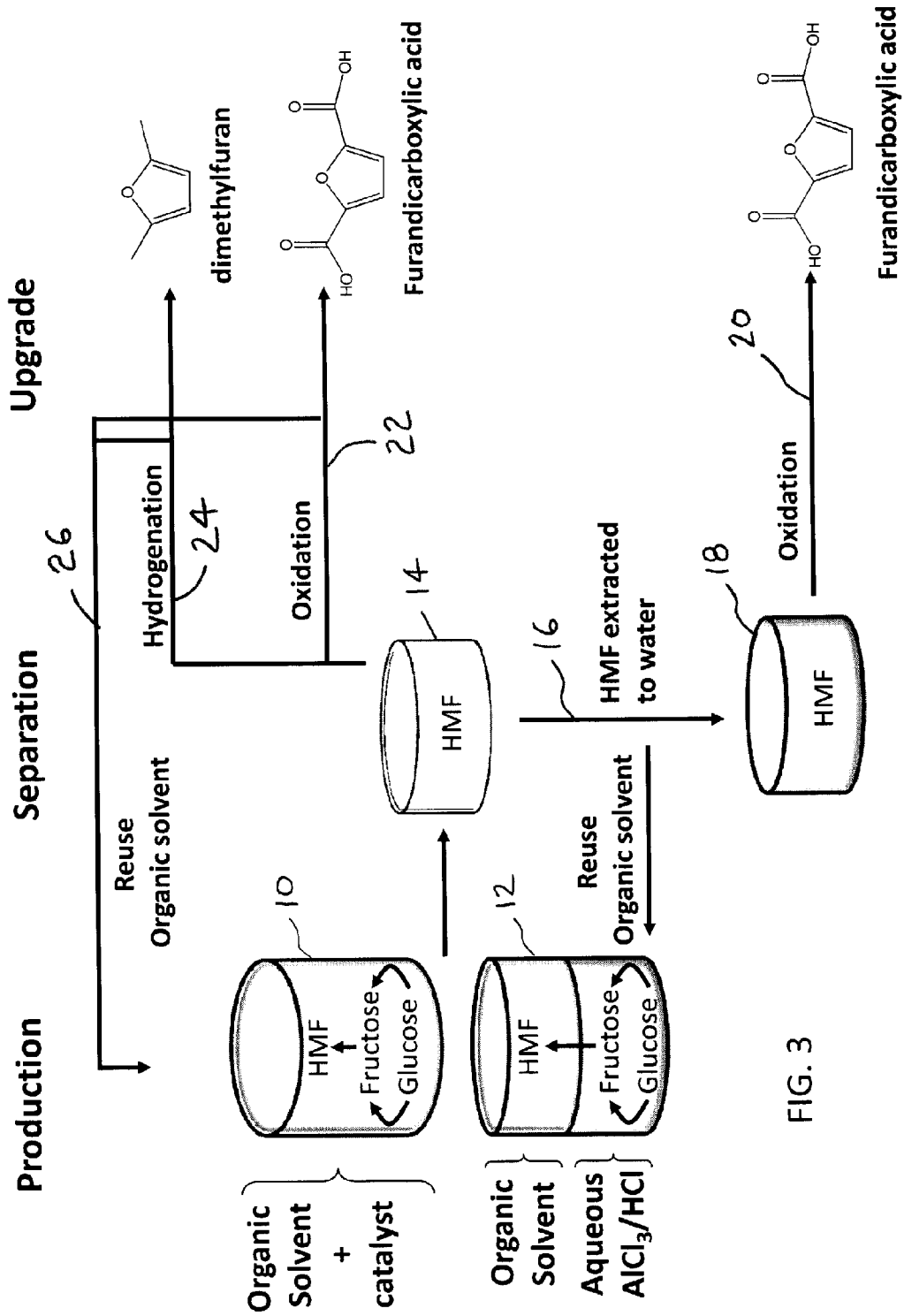
FIG. 3 is a schematic overview of the process of using organic solvent derived from biomass to convert C6 sugars from biomass (typically glucose and fructose) into HMF and other downstream, value-added chemicals.

Overview and Schematic Depiction of Reaction Types:

FIG. 3 depicts a schematic overview of the process to produce HMF, as well as to upgrade the HMF to value-added, downstream chemicals such as dimethylfuran (DMF) and furandicarboxylic acid (FDCA). As shown in FIG. 3, the production of HMF can take place in either a monophasic reaction solution 10 or in a biphasic reaction solution 12 having an aqueous reaction phase and an organic extraction phase. Both approaches will be discussed in greater detail below. In both approaches, and acid catalyst is used and the organic solvent itself is derived from biomass. It is preferred that the organic solvent in either 10 or 12 be a lactone, a hydrofuran or a hydropyran as defined herein, and most preferably a gamma-lactone that can be, but not only, derived from a corresponding C5 to C16 carboxylic acid (i.e., gamma valerolactone to gamma hexadecalactone) and tetrahydrofuran that can be obtained, but not only, from furfural.

In reactors 10 and 12, biomass-derived C6 sugars are converted to HMF. The HMF formed in reactor 10 or 12 may be concentrated, separated or otherwise purified at 14. If the HMF remains admixed with organic solvent, the HMF may be extracted 16 into water to yield an aqueous solution of HMF 18. From here, the aqueous solution of HMF 18 may be oxidized 20 to yield FDCA. The organic solvent that spontaneously phase separates from the aqueous solution of HMF may be recycled into reactor 12. Alternatively, the HMF at 14 may be directly oxygenated 22 or hydrogenated 24, with or without any intervening steps, to yield downstream products such as dimethylfuran or FDCA. The organic solvent may be captured and recycled into reactor 10 or 12 as shown at 26.

Figure 4:
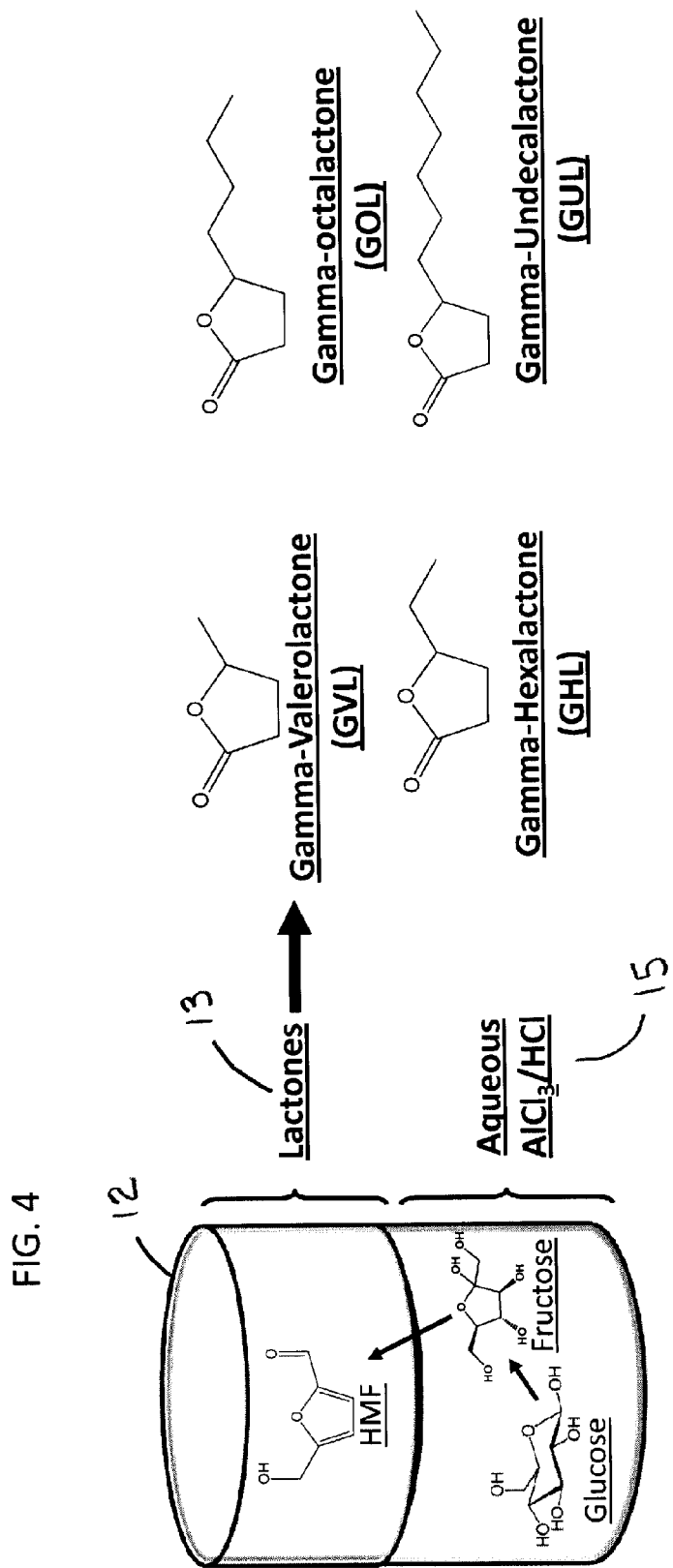
FIG. 4 is a schematic diagram of a first version of the process in which a biphasic reaction is used to produce HMF from C6 sugars derived from biomass. The upper, organic layers comprises one or more lactones, such as (and without limitation) gamma-valerolactone (GVL), gamma-octolactone (GOL), gamma-heaxlactone (GHL), and gamma-undecalactone (GUL).

FIG. 4 is an isolated view of reactor 12 as shown in FIG. 3. Here, the reaction to yield HMF takes place in a biphasic system comprising a lower aqueous phase 15 and an upper organic phase 13 that comprises a lactone, preferably a biomass-derived lactone, more preferably a biomass-derived gamma-lactone, and most preferably biomass-derived GVL, GHL, GOL, and/or GUL. As shown in FIG. 4, biomass-derived glucose isomerizes to fructose and is then converted to HMF in the presence of an acid catalyst in the aqueous phase 15. The HMF so formed then is extracted into lactones in the organic phase 13.

Figure 5:
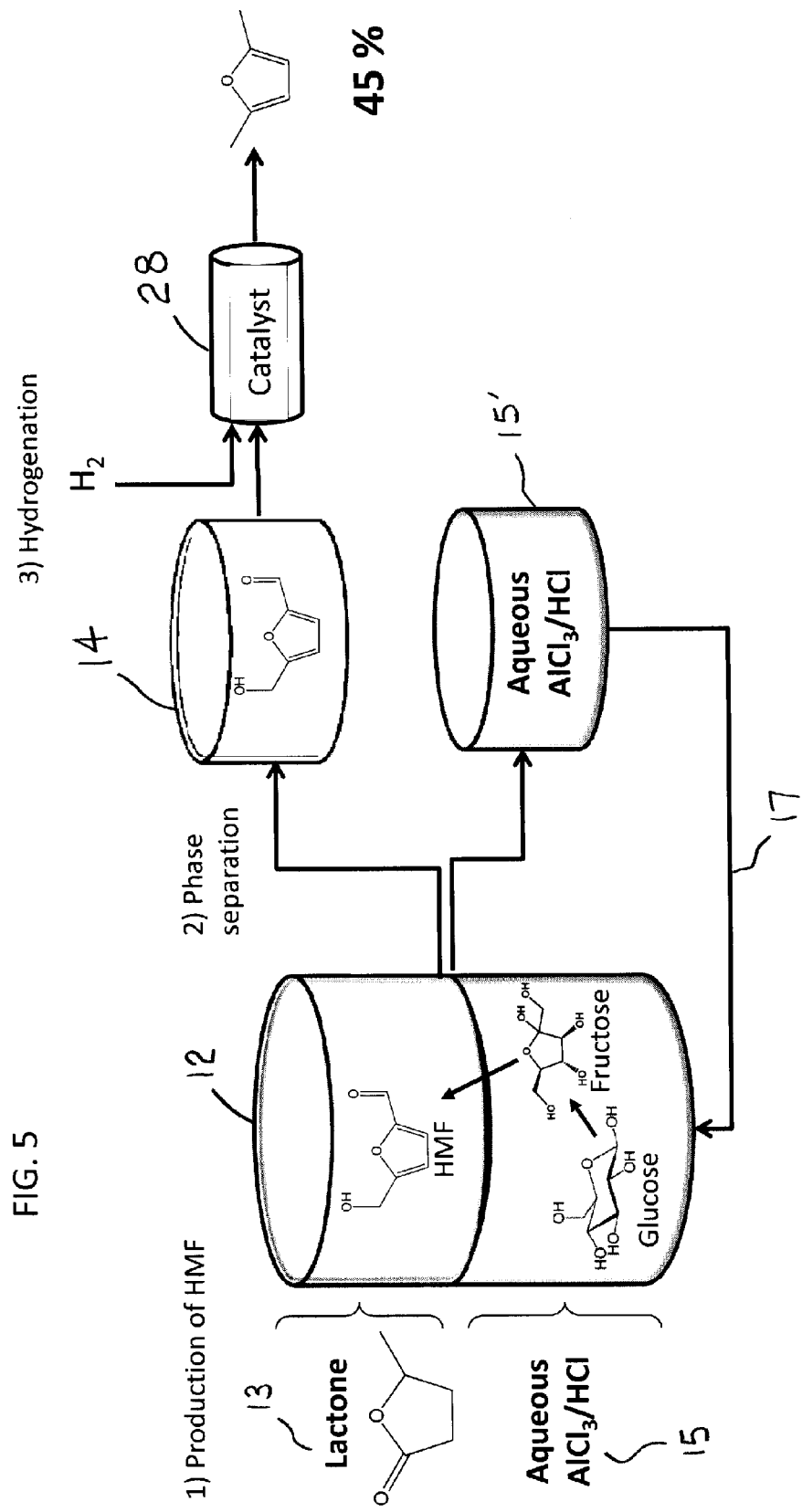
FIG. 5 is a schematic diagram as depicted in FIG. 4, and further depicting downstream hydrogenation of the HMF to yield 2,5-dimethylfuran (b.p. ~95° C.; considerably lower than b.p. of GVL, ~208° C.).

FIG. 5 is an isolated view of the process using a biphasic reactor 12 and a hydrogenation catalyst 28 to convert C6 sugars to HMF and to convert the HMF to dimethylfuran. As in FIG. 4, the reaction to yield HMF takes place in a biphasic system comprising a lower aqueous phase 15 and an upper organic phase 13 that comprises a lactone (as described previously). C6 sugars in the aqueous phase are converted to HMF which is then extracted into the lactone-containing organic phase 13. The two phases are then separated to yield an organic phase 14 containing the HMF and an aqueous phase 15' containing water and the acid catalyst. The HMF at 14 is then subjected to a hydrogenation reaction using a hydrogenation catalyst 28 to yield dimethylfuran as the product. Yields of 45% and better are typical.

Figure 6:
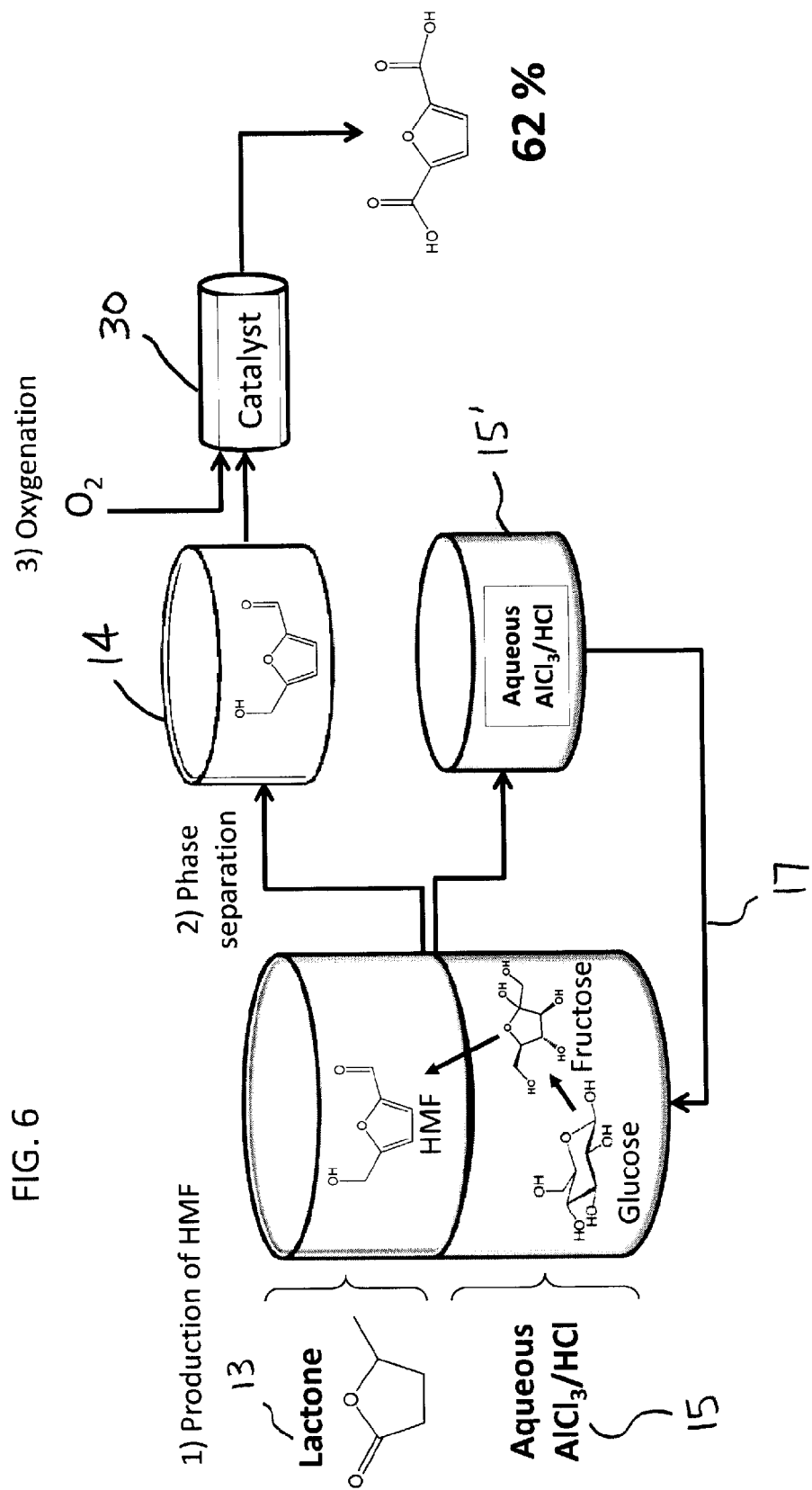
FIG. 6 is a schematic diagram as depicted in FIG. 4, and further depicting downstream oxygenation of the HMF to yield 2,5-furandicarboxylic acid (FDCA).

FIG. 6 is identical to FIG. 5, with the exception that rather than hydrogenating the HMF, the HMF is oxidized over an oxygenation catalyst 30 to yield FDCA. Yields of 62% and better are typical. Thus, the reaction to yield HMF takes place in a biphasic system comprising a lower aqueous phase 15 and an upper organic phase 13 that comprises a lactone. C6 sugars in the aqueous phase are converted to HMF which is then extracted into the lactone-containing organic phase 13. The two phases are then separated to yield an organic phase 14 containing the HMF and an aqueous phase 15' containing water and the acid catalyst. The HMF at 14 is then subjected to the oxygenation reaction 30.

Figure 7:
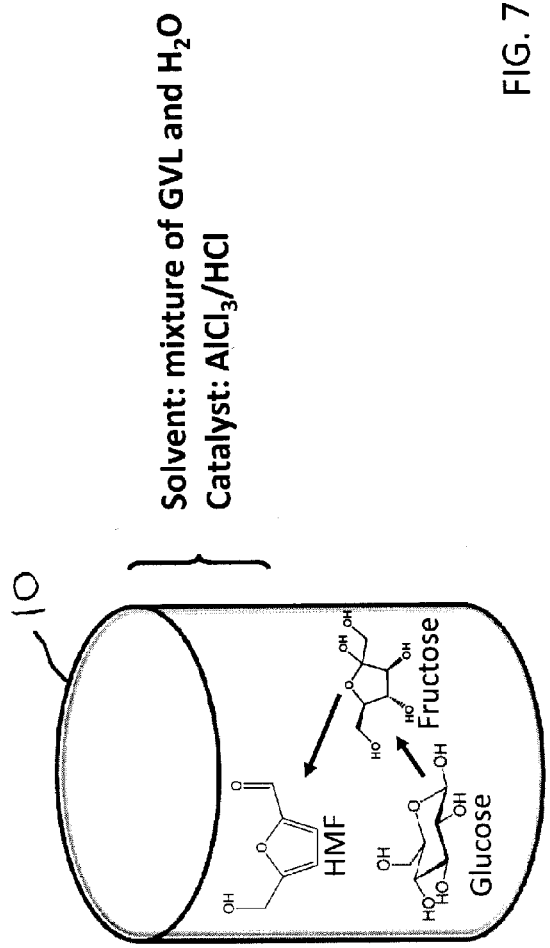
FIG. 7 is a schematic diagram of a second version of the process in which a monophasic reaction using homogeneous catalysts is used to produce HMF from C6 sugars derived from biomass.

FIG. 7 is an isolated view of reactor 10 as shown in FIG. 3. Here, the reaction to yield HMF takes place in a monophasic system comprising a lactone, a hydrofuran or a hydrofuran that is miscible with water or has at least 5% solubility in water. FIG. 7 exemplifies the use of the gamma-lactone GVL, which is miscible with water and can be obtained from biomass. For illustration purposes only, the acid catalyst is depicted as $AlCl_3$ and HCl. As noted in the figure a number of advantages are realized by using a monophasic system. Homogeneous and/or heterogeneous catalysts may be used. There are no mixing concerns because the reaction solution is monophasic. HMF is obtained in very high yields. The GVL solvent (was well as other suitable lactones, hydrofurans, hydropyrans) have very low toxicity.

Figure 8:
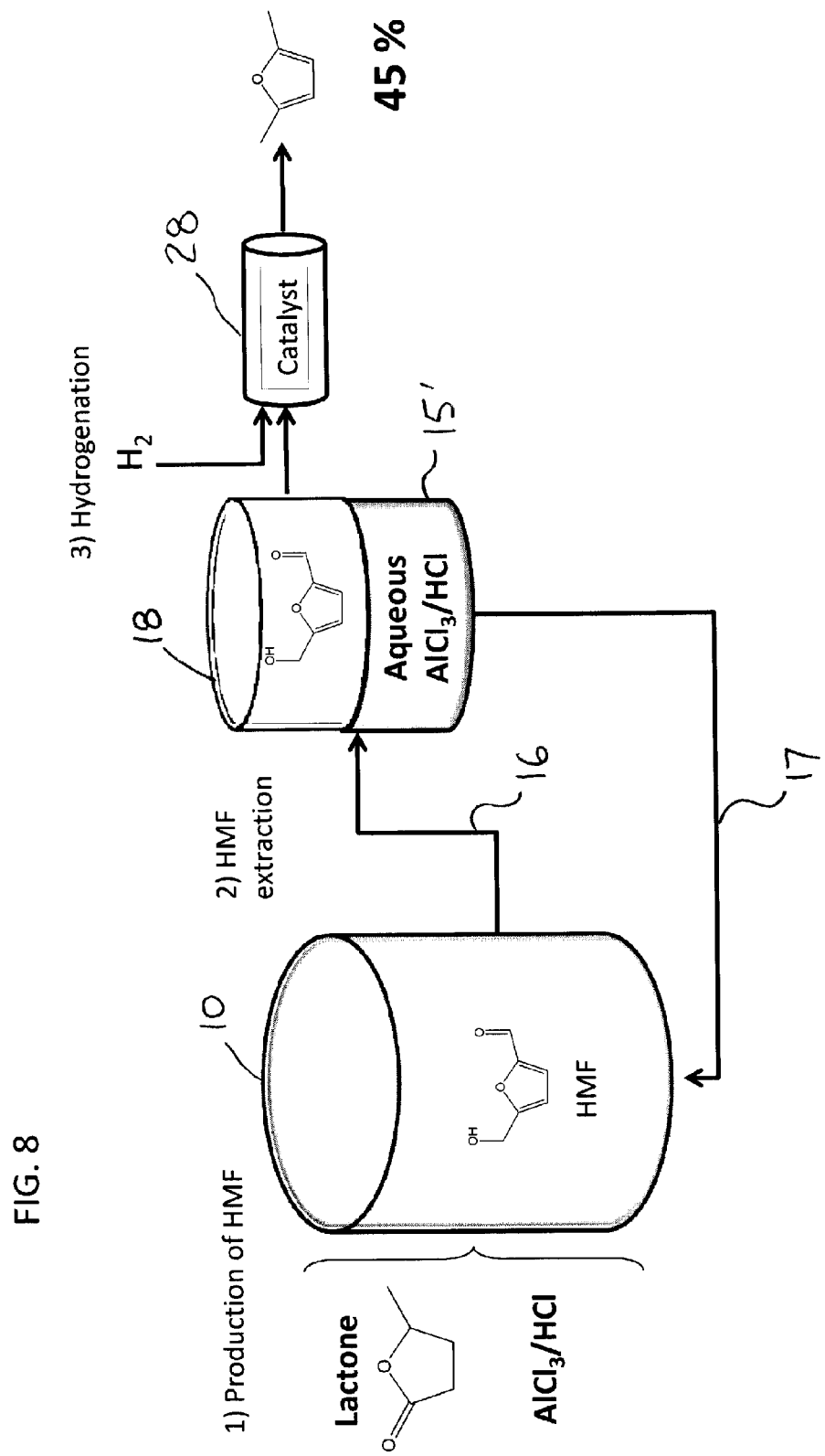
FIG. 8 is a schematic diagram as depicted in FIG. 7, and further depicting downstream hydrogenation of the HMF to yield 2,5-dimethylfuran.

A schematic diagram depicting using the monophasic reaction system to make dimethylfuran from biomass-derived sugars is shown in FIG. 8. Here, reactor 10, as described in FIG. 7 is used to produce HMF from glucose/fructose, as described previously. For illustration purposes only, in FIG. 8, the lactone in reactor 10 is depicted as GVL, and an AlCl$_3$/HCl acid catalyst is utilized. The HMF is then extracted 16 into an organic phase 18 and an acidic, aqueous phase 15'. The HMF present in phase 18 can then be hydrogenated using hydrogenation catalyst 28 to yield dimethylfuran. The aqueous, acidic phase 15' may optionally be recycled 17 back into reactor 10.

Figure 9:
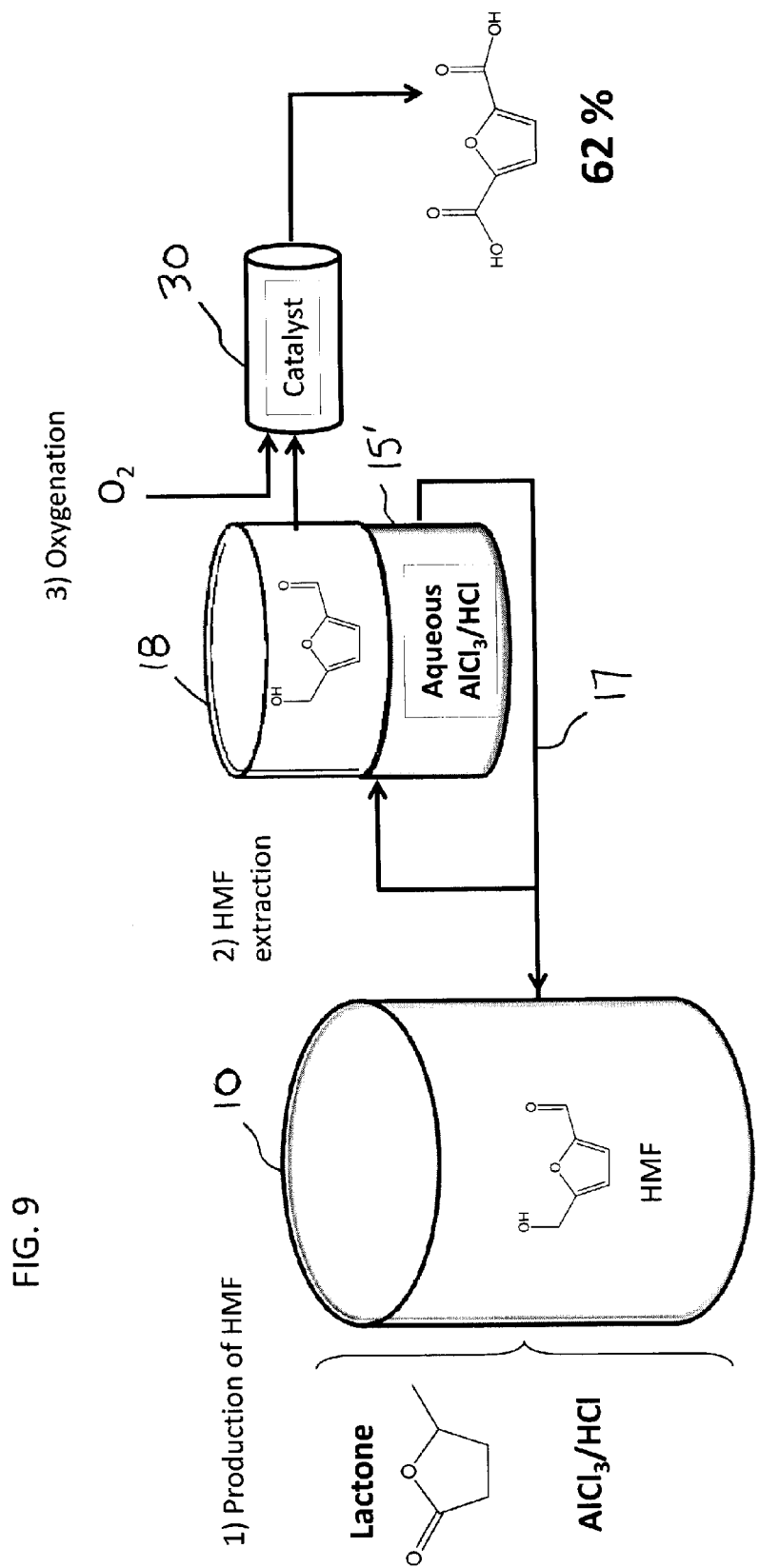
FIG. 9 is a schematic diagram as depicted in FIG. 7, and further depicting downstream oxygenation of the HMF to yield FDCA.

In similar fashion, FIG. 9 depicts schematically the same reaction as depicted in FIG. 8, with the exception that the HMF formed is oxygenated over an oxygenation catalyst 30 to yield FDCA. Thus, reactor to is used to produce HMF from glucose/fructose in a monphasic system. The exemplary lactone depicted as GVL, and an exemplary AlCl$_3$/HCl acid catalyst is also shown. The HMF is then extracted 16 into an organic phase 18 and an acidic, aqueous phase 15'. The HMF present in phase 18 is then oxidized using catalyst 30. The aqueous, acidic phase 15' may optionally be recycled 17 back into reactor 10.

Figure 10:
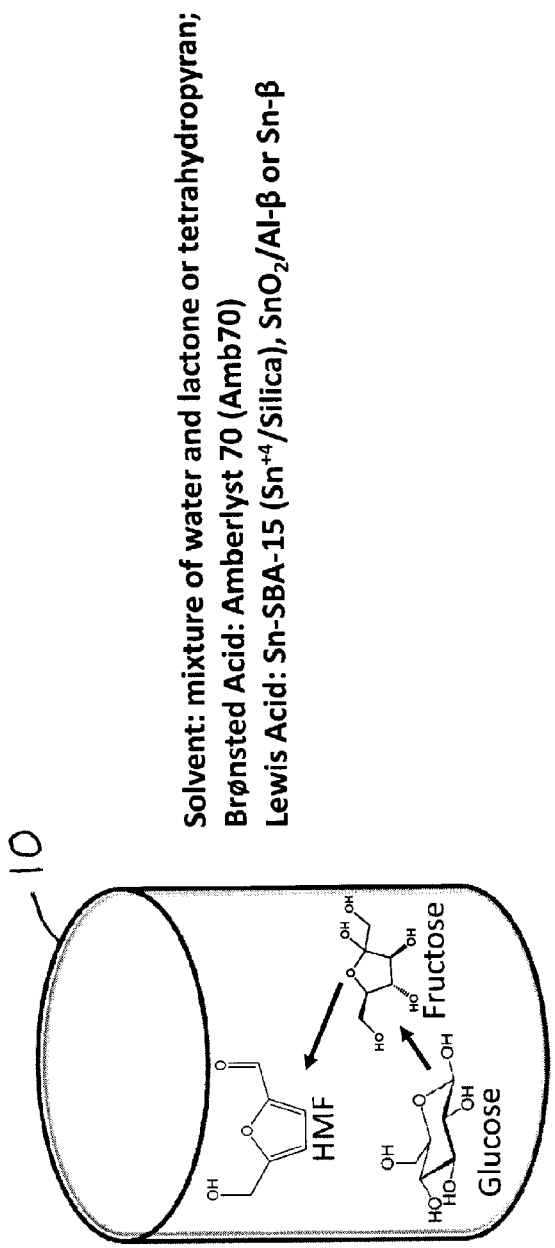
FIG. 10 is a schematic diagram of a third version of the process in which a monophasic reaction using heterogeneous catalysts is used to produce HMF from C6 sugars derived from biomass.

FIG. 10 is identical to FIG. 7, with the exception that a solid acid catalyst (i.e., a heterogeneous catalyst) is used. Again, the reaction solvent comprises a monophasic solution of a lactone and water. One or more solid acid catalysts are used to drive the formation of HMF from sugars in the reactant solution. Exemplary solid acid catalysts are noted in the figure. On top of the advantages listed in FIG. 7, using solid acid catalysts as depicted in FIG. 10, in conjunction with a monophasic reaction, means there is no need of phase separations and the solid acid catalysts are easily removed by simple filtration.

Figure 11:
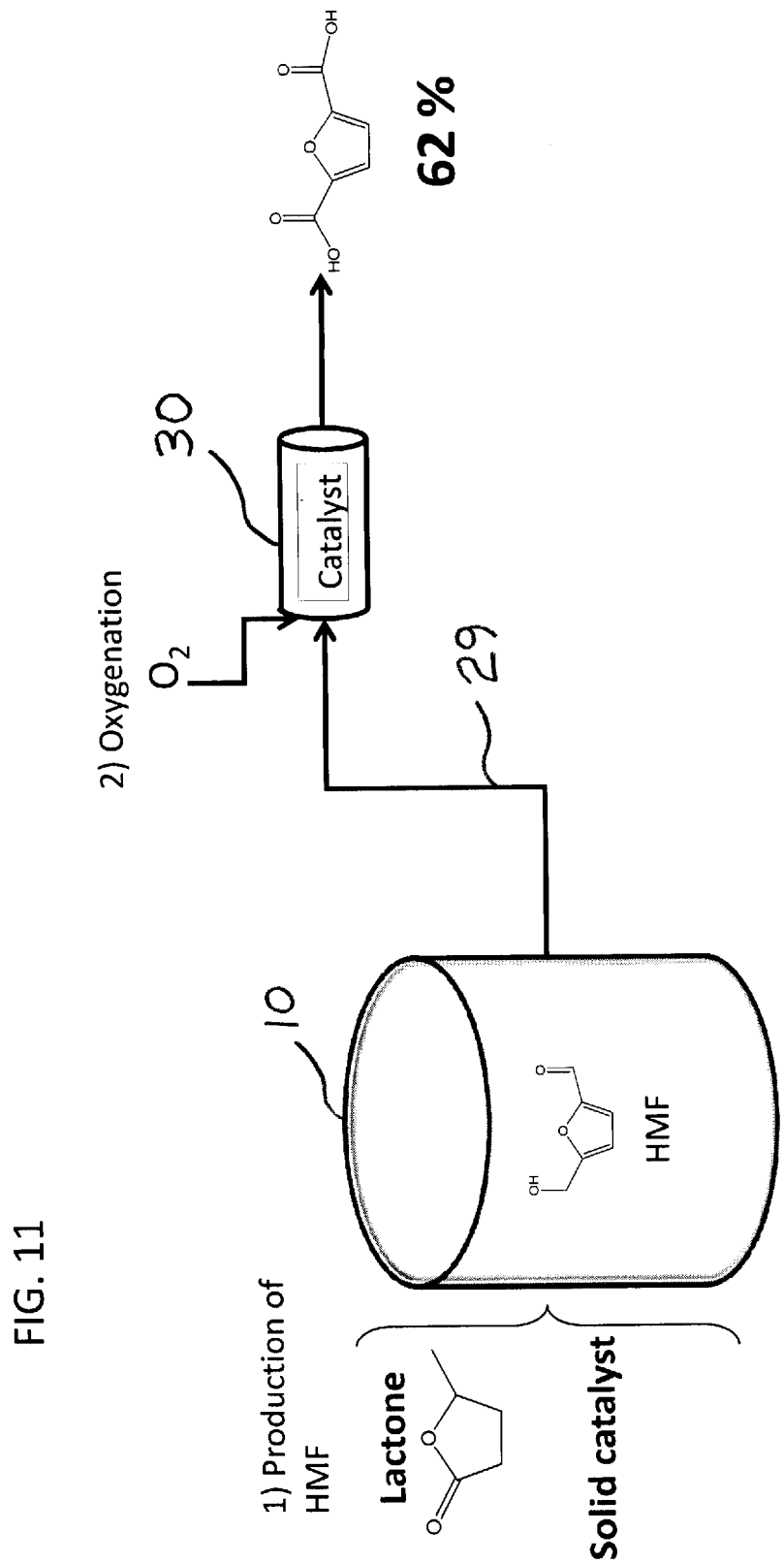
FIG. 11 is a schematic diagram as depicted in FIG. 10, and further depicting downstream oxygenation of the HMF to yield FDCA.
Figure 12:
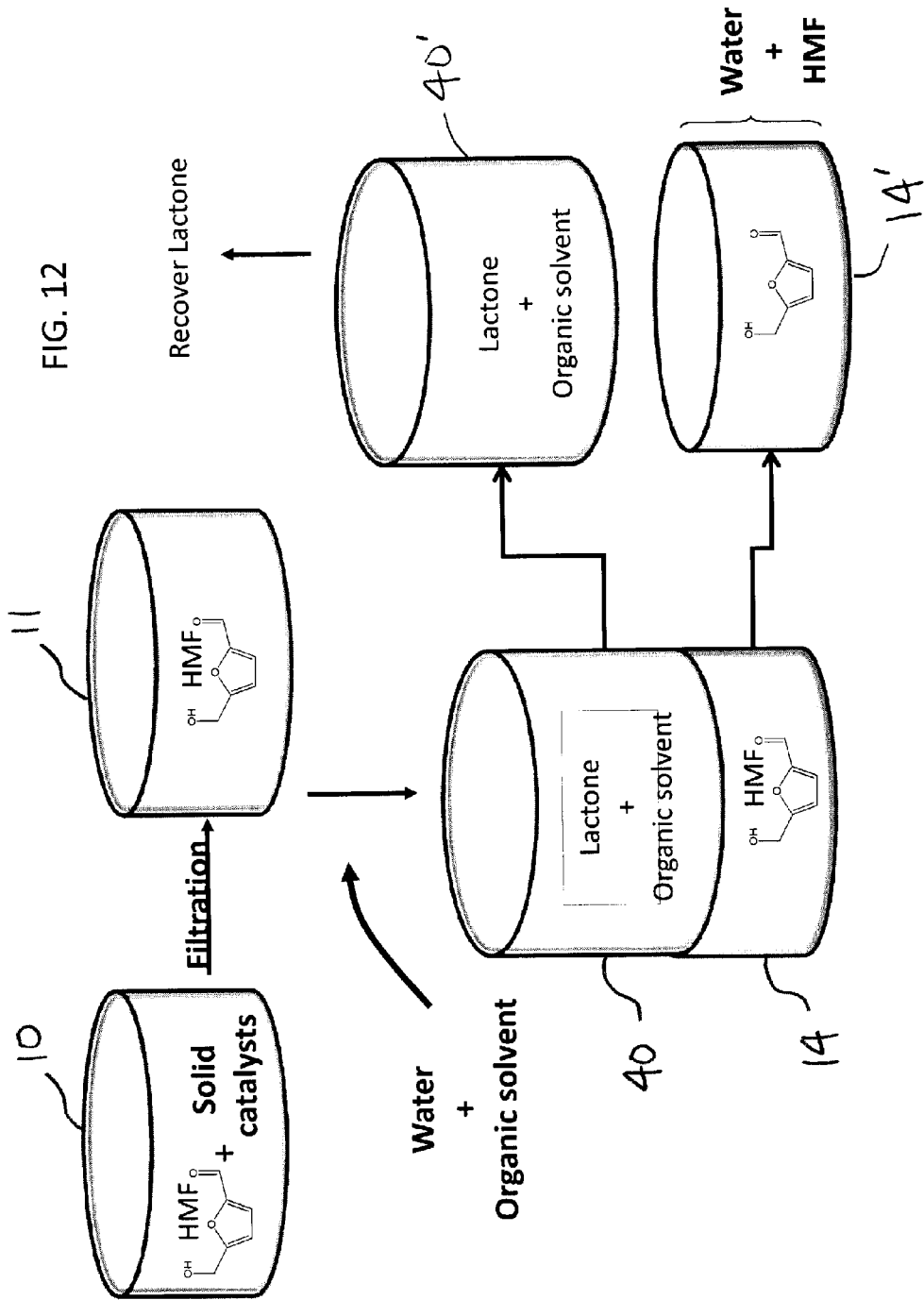
FIG. 12 is a schematic diagram as depicted in FIG. 10, and further depicting downstream extraction of the HMF into an aqueous solution.
Figure 13:
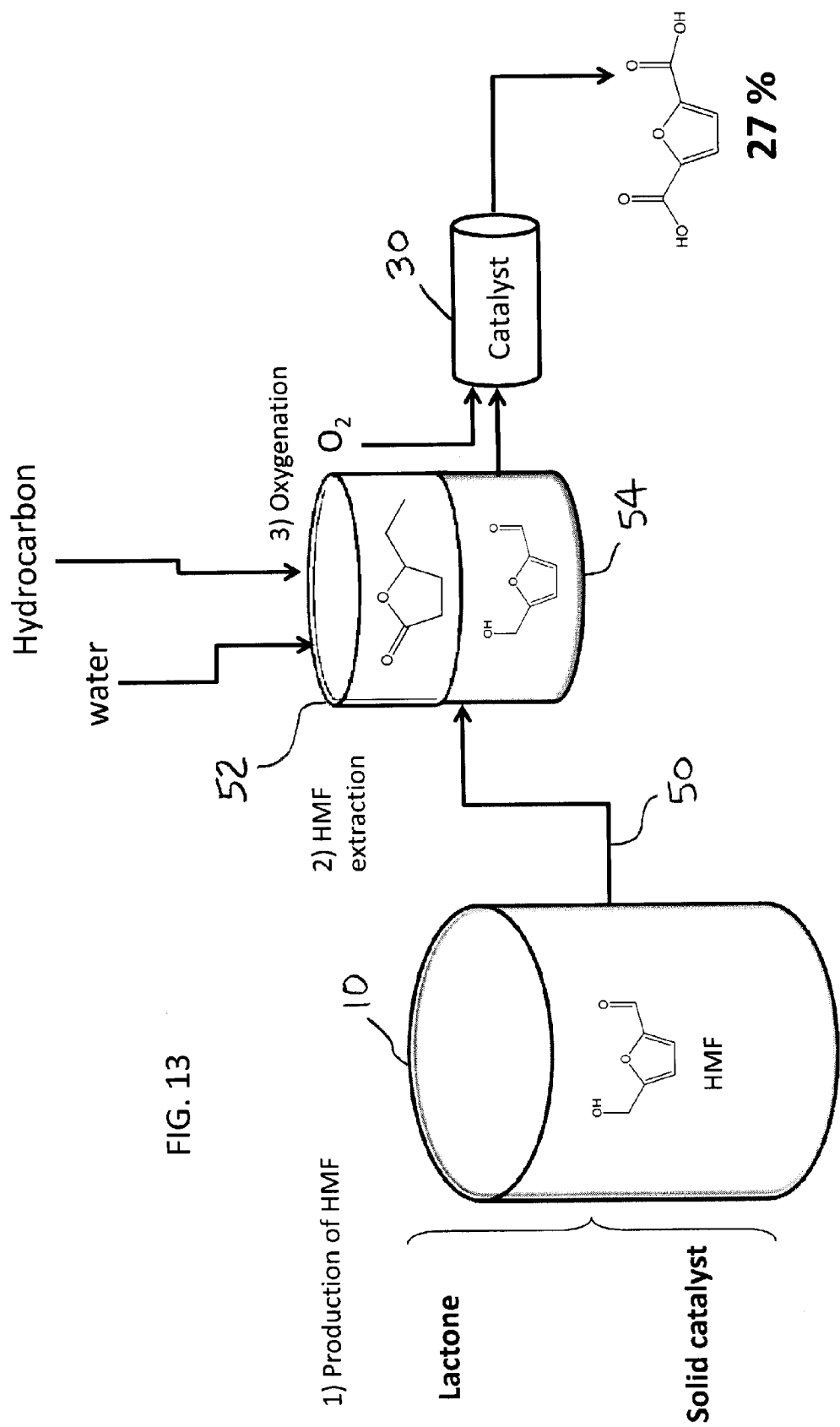
FIG. 13 is a schematic diagram of depicting oxidation of HMF present in the aqueous phase of a biphasic system to yield FDCA.

This enables very efficient reactions to yield HMF and downstream products, such as the reactions shown in FIGS. 11, 12 and 13. In FIG. 11, the HMF is formed in the monophasic solution using a solid acid catalyst as described herein. The catalyst is then easily removed and the HMF solution transferred via conduit 29 to contact an oxygenation catalyst to yield FDCA.

Alternatively, as shown in FIG. 12, a similar approach using solid acid catalysts may be used to yield an aqueous solution of HMF as the final products. Here, the HMF is formed from biomass-derived sugars in a lactone-containing, monophasic solvent using a solid acid catalyst 10. The solid catalyst is then removed by filtration to yield the HMF in a lactone-containing solvent 11. A mixture of water and an organic solvent is then added to 11 to cause a spontaneous phase separation in which the HMF is extracted into the aqueous phase. The two phases are then separated to yield an aqueous solution of HMF 14' and an organic solution containing the lactone 40'. The lactone may optionally be recovered and recycled back into reactor 10.

FIG. 13 depicts the same approach as described for FIG. 12, with the added downstream step of converting the HMF in the aqueous phase 54 to FDCA using an oxygenation catalyst 30. Thus, in FIG. 13, the HMF is formed from biomass-derived sugars in a lactone-containing, monophasic solvent using a solid acid catalyst 10. The solid catalyst is the removed by filtration (50) and water and an organic solvent (shown as "hydrocarbon" in FIG. 13) are then added to cause a spontaneous phase separation in which the HMF is extracted into an aqueous phase 54 and a lactone-containing organic phase 52. The HMF is then oxidized at 30 to yield FDCA.

EXAMPLES

The following examples are included solely to provide a more complete description of the process described and claimed herein. The examples do not limit the scope of the process in any fashion.

Solvents and Catalysts Used:

Table 1 depicts the various organic solvents that were used in the examples. Note that the list of solvents is exemplary and not limiting.

TABLE 1

Solvents used in the examples.

| Solvent name | Abbreviation | Structure |
|---|---|---|
| Gamma-valero-lactone | GVL | 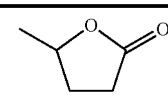 |
| Gamma-hexa-lactone | GHL | 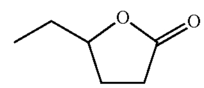 |
| Gamma-octa-lactone | GOL | 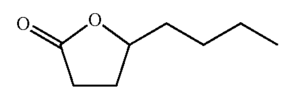 |
| Gamma-undeca-lactone | GUL | 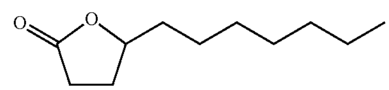 |
| Tetrahydro-furan | THF | 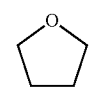 |
| sec-Butyl-phenol | SBP | 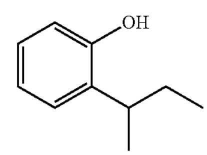 |

Brønsted Solid Acid Catalysts:

"AMBERLYST"-70®-brand solid acid catalyst were obtained from The Dow Chemical Company (Midland, Mich., USA). "AMBERLYST"-brand resins are a family of commercial catalysts comprising a backbone of cross-linked polystyrene modified with sulfonic acid groups. "AMBERLYST" is a registered trademark of Rohm and Haas Company, Philadelphia, Pa. (a wholly owned subsidiary of The Dow Chemical Company).

Lewis Acid Catalysts:

Sn-SBA-15: Synthesized as described by Shah et al. [39]. SBA-15 is a mesoporous structure of amorphous silica. Tin cations were inserted in tetrahedral positions into the silica framework in a ratio Si/Sn=40.

SnO$_2$/Al-β: Al-β Zeolite is a crystalline microporous aluminosilicate mineral that possesses well defined structure type with distinct pore dimensions and pore connectivity. The presence of aluminum in tetrahedral positions generated negative structural charges that are counterbalanced, in this specific case, by protons. The protons in Al-β Zeolite (Zeolyst) were exchanged with tin cations, followed by calcinations.

Sn-β (Haldor Topsoe, A/S, Denmark): Presents similar structure to Al-β Zeolite, but contains structural Sn atoms instead of aluminum. Tin is tetrahedrally coordinated to the zeolite structure, but differently from aluminum, does not generated structural charges.

Suitability of Biomass-derived Solvents:

Biphasic Reactors Using γ-Lactones as Extracting Layer and Homogeneous Catalysts:

Biphasic dehydration reactions were carried out in 10 mL thick-walled glass reactors heated in an oil bath at 170° C. Preparation of the aqueous layer comprised using solutions containing 5 mmol $L^{-1}$ $AlCl_3$ and adjusting their pH to 2.5 with HCl. The pH-adjusted solutions were saturated with NaCl, and cellulose or monosaccharide was added to obtain a 5 wt. % aqueous feed. In a typical experiment, 1.5 g of the aqueous feed and 3.0 g of γ-lactone were added to the reactor. The reactor was placed in the oil bath at 170° C. and stirred at 1000 rpm. Reactors were removed from the oil bath at specific reaction times and cooled in an ice-water bath.

In biphasic reactors using GVL as organic extracting layer, glucose and fructose can be converted to HMF in high selectivity.

Systems using GHL and GOL as an organic extracting layer produce HMF with selectivities comparable to that observed for GVL.

The system using GUL is less selective in the formation of HMF. To evaluate using γ-lactones and THF as biomass-derived solvents for conversion of biomass, cellulose or C6 monossacharides into HMF, a biphasic system was employed. See FIG. 4. In the biphasic reaction, substrates reaction takes place in the aqueous layer 15, followed by the extraction of HMF into the organic layer 13, where it is protected from catalysts, thus minimizing side reactions. The aqueous layer 15 must be saturated with NaCl to diminish the solubility of both the organic solvent and HMF, improving the efficiency of the organic extracting layer. As shown in FIG. 4, aluminium chloride was used as isomerization catalyst, and HCl was used as the dehydration catalyst. The upper organic layer, 13, comprised lactones (GVL, GHL, GOL, and GUL) derived from biomass.

TABLE 2

Conversion of cellulose, glucose or fructose to HMF in a biphasic system with γ-lactones, THF and SBP as the extracting organic layer.†

| Feed | Organic Layer | Time/min | Conv./% | Selec./% | % HMF in Org Layer | % HCl in Aq. Layer |
|---|---|---|---|---|---|---|
| Fructose | GVL | 20 | 94 | 84 | 94 | 30 |
| Glucose | GVL | 40 | 88 | 70 | 94 | 30 |
| Cellulose | GVL | 360 | 100 | 34 | 94 | 30 |
| Glucose | GHL | 40 | 88 | 65 | 92 | 20 |
| Glucose | GOL | 40 | 89 | 65 | 92 | 10 |
| Glucose | GUL | 40 | 92 | 54 | 83 | 0 |
| Glucose | THF [Ref 6] | — | 80 | 71 | 93 | 30 |
| Glucose | SBP [Ref 6] | 40 | 91 | 68 | 97 | 0 |

†Reaction conditions: 1.5 g of aqueous feed (5 wt % cellulose, glucose, or fructose, 5.0 mmol $L^{-1}$ $AlCl_3$ and 3.17 mmol $L^{-1}$ HCl); 3.0 g of organic solvent; T = 170° C.

As seen in the results presented in Table 2, the selectivity for conversion of glucose to HMF using the γ-lactones in a biphasic system (with the exception of GUL) are comparable with systems using THF and SBP as the extracting solvent. (See the final entry of Table 2). However, the γ-lactones extract a portion of the HCl from the aqueous layer. This does not render the process inoperable, but can impact HMF separation or upgrading. It also tends to increase process cost because the aqueous layer has to be re-acidified and the organic layer has to be neutralized. For example, the molar ratio of "HMF formed"-to-"HCl lost" is approximately 200 when using THF and GVL as the extracting solvents.

HCl Balance:

As mentioned before, one important aspect in the biphasic reactors is the extraction of the homogeneous catalysts by the organic layer. By titration of aqueous and organic layers, it was found that GVL and GHL can extract, respectively 30 and 20% of the HCl from the aqueous layer. Aqueous layers were directly titrated with a 0.01 mol L-1 sodium hydroxide solution using phenolphthalein as indicator. Organic layers were contacted with water to extract the HCl before titration.

Recycle of the System Using GHL as Organic Extracting Layer:

Experimental: For recycle experiments, an aqueous solution with 5 mM $AlCl_3$ was first prepared and adjusted to a pH of 2.5 with HCl. This mixture was saturated with NaCl, glucose was added to reach 5 wt %, and 1.5 g of the aqueous feed was added to a 10 mL thick-walled glass reactor containing 3.0 g of GHL. The reactor was heated in an oil bath to 443 K with stifling at 1000 rpm for 40 min. Upon completion of the reaction, reactors were cooled. The organic layer was extracted and glucose added to the remaining aqueous layer to obtain a 5 wt % glucose mixture. Fresh GHL was added to the reactor, and the reaction was carried out for consecutive runs, as described above.

TABLE 3

Conversion and selectivity for production of HMF from glucose in consecutive runs using GHL as extracting organic layer.ᵃ

| Run | Feed | Lactone | Time/min | Conversion/% | Selectivity/% |
|---|---|---|---|---|---|
| 1 | Glucose | GHL | 40 | 88 | 65 |
| 2 | Glucose | GHL | 40 | 85 | 68 |
|   | Glucose | GHL | 50 | 90 | 67 |
| 3 | Glucose | GHL | 40 | 66 | 66 |
|   | Glucose | GHL | 60 | 89 | 67 |
| 4 | Glucose | GHL | 40 | 65 | 68 |
|   | Glucose | GHL | 50 | 88 | 67 |

ᵃReaction conditions: 1.5 g of aqueous feed (5 wt % glucose, 5 mM $AlCl_3$ at pH to 2.5), 3.0 g of lactone; Temperature 443 K.

For recycling, the organic layer was extracted and glucose added to the remaining aqueous layer to obtain a 5 wt % glucose mixture. Fresh GHL was added to the reactor, and the reaction was carried out for consecutive runs, as described above.

As observed in Table 3, for reusing the aqueous layer, it is necessary to increase the reaction time by 10 min after each reuse. This is a consequence of the extraction of a portion of the catalyst from the aqueous to the organic layer.

Monophasic Reactors Using Lactones, Hydrofurans or Hydropyrans with 10% of Water and Homogeneous Catalysts:

Of the solvents listed in Table 2, THF, GVL, and GHL can form a monophasic mixture with water. THF and GVL are miscible in water, while GHL can dissolve 7-10 wt % of water. The use of monophasic solvent systems alleviates potential mixing inefficiencies that may be encountered when scaling up biphasic systems.

Accordingly, the next set of reactions explored was the production of HMF from biopmass, cellulose or C6-sugar in a monophasic solvent system comprising of GVL, GHL, and/or THF with 10 wt % water using $AlCl_3$ and HCl as catalysts. (These reactions are depicted schematically in FIG. 7-10.) As shown in Table 4, the results obtained in these monophasic systems are similar to those shown in Table 1.

TABLE 4

Conversion of cellulose, glucose, or fructose to HMF in a monophasic system with THF or γ-lactones and 10 wt. % water.†

| Feed | Organic Solvent | Time/min | Conversion/% | Selectivity/% |
|---|---|---|---|---|
| Glucose | GVL | 20 | 89 | 66 |
| Cellulose | GVL | 130 | 100 | 31 |
| Glucose | GHL | 20 | 90 | 65 |
| Glucose | THF | 20 | 90 | 56 |

†Reaction conditions: 1.5 g of organic solvent:water (9:1); feed = 2 wt % cellulose or glucose, 5.0 mmol L$^{-1}$ AlCl$_3$, and 3.17 mmol L$^{-1}$ HCl; T = 170° C.

Monophasic Reactors Using Lactones, Hydrofurans or Hydropyrans with 20% of Water and Homogeneous Catalysts:

Experimental: In 10 mL thick-walled glass reactors were added 0.294 g of a 25 mM AlCl$_3$ aqueous solution with pH adjusted to 1.8 with HCl, 1.176 g of organic solvents and 0.03 g of cellulose or monosaccharide. The final concentrations were 2 wt % of cellulose or monosaccharide; 5 mM of AlCl$_3$; 3.2 mM of HCl. The weight ratio water:organic solvent is 1:4. The reactor was placed in the oil bath at 443 K and stirred at 700 rpm. Reactors were removed from the oil bath at specific reaction times and cooled in an ice-water bath.

TABLE 5

Conversion of cellulose, glucose or fructose to HMF in a monophasic reactor with using lactones or THF and water in a ratio 4:1.$^a$

| Feed | Solvent | Time/min | Conversion/% | Selectivity/% |
|---|---|---|---|---|
| Fructose | GVL | 9 | 90 | 81 |
| Glucose | GVL | 20 | 89 | 66 |
| Cellulose | GVL | 130 | 100 | 31 |
| Glucose | THF | 20 | 90 | 56 |

$^a$Reaction conditions: 1.5 g of feed (5 wt % cellulose, glucose or fructose, 5 mM AlCl$_3$ at pH to 2.5; water:organic solvent ratio of 1:4); Temperature 443 K.

In the monophasic reactors with a GVL:water weight ratio of 4:1, the selectivities for HMF obtained from cellulose, glucose or fructose are similar to those observed in the biphasic reactor.

The System Using THF Presents Performance Inferior to that Using GVL

In these monophasic systems, the homogeneous catalysts can be substituted for heterogenous catalysts.

An advantage of using monophasic systems (as contrasted to a biphasic systems) is that the addition of salt is not necessary (as it is to achieve a biphasic system with these same lactone solvents). This allows for replacing the homogeneous catalysts used for glucose isomerization and fructose dehydration with solid acid catalysts.

Heterogeneous Isomerization Catalysts:

To establish the most appropriate heterogeneous isomerization catalyst for glucose isomerization, a leaching test was performed for Sn-β (Si:Sn=400), Sn-SBA-15 (Si:Sn=40) and hydrotalcite. For this test, 0.1 g of catalyst was stirred in a mixture GVL:H$_2$O (9:1) for 30 min at 130° C. The catalyst was removed by filtering, and glucose was added to the solvent to make a 2 wt. % sugar solution. The mixture was stirred for 30 min at 130° C. Conversion of glucose was only observed in the solution contacted with hydrotalcite, indicating leaching.

The solid Brønsted acid catalyst used in the Examples of the monophasic reactor systems was Amberlyst 70 (Amb-70), a sulfonic acid-functionalized catalyst. Other solid acid catalyst may also be used in the process, such as zeolites (mordenite, ZSM-5, Z-Y, USY and Z-β), cubic and amorphous zirconium phosphate, titanium oxide, niobium oxide, phosphated niobic acid, etc. A previous study showed low deactivation of Amb-70 in the dehydration of fructose at 130° C. in a flow reactor system using THF:H$_2$O (4:1) as solvent. [10]

Figure 14:
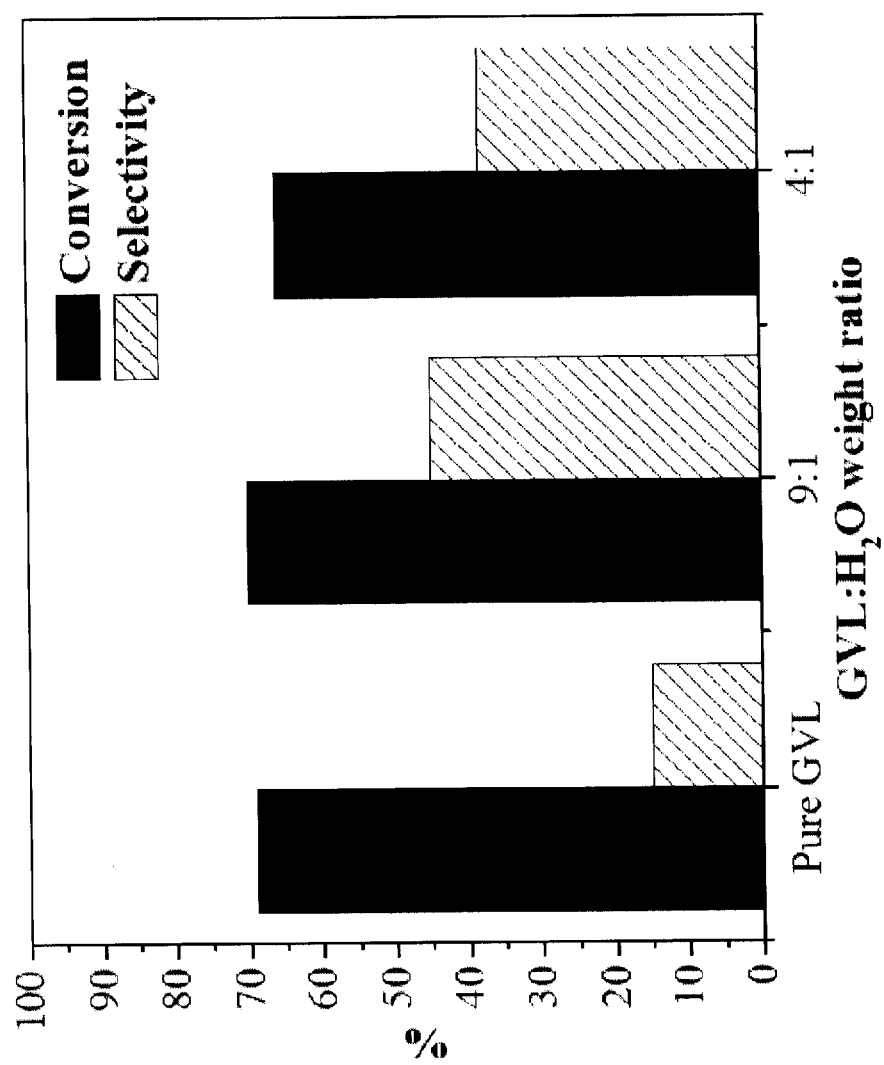
FIG. 14 is a histogram depicting the effect of water content on glucose conversion to HMF using the present process.

Effect of Water:

Because water is produced during glucose conversion to HMF, and the presence of water increases the solubility of glucose, the effect of water concentration was studied in the conversion of glucose to HMF using GVL as the solvent and Amb-70 and Sn-SBA-15 as catalysts. Although water is known to promote side reactions in the dehydration of sugars, [14] it can be seen in the unexpected results from FIG. 14 that water is beneficial in low concentrations, roughly less than about 20% and preferably between about 2% and about 15%, most preferably between about 2% and about 12% water. At similar conversion (~70%), the system with mass ratio GVL:H$_2$O (9:1) showed higher HMF selectivity than those with a GVL:H$_2$O ratio of 4:1 or pure GVL.

Table 6 shows the results for conversion of fructose and glucose to HMF using Amb-70 or a combination of Amb-70 and Sn-based catalysts (Sn-β or Sn-SBA-15) in GVL, GHL or THF containing 10 wt % water. These experiments were carried out for different catalysts and solvents at similar conversions (~90%). It can be seen that HMF was obtained from fructose using Amb-70 with selectivities between 80 and 85%. Direct dehydration of glucose using Amb-70 led to selectivities lower than 35%, in agreement with early reports showing that direct dehydration of glucose with mineral acids leads to low selectivity to HMF. [6, 30] The combination of a Sn-based catalyst and Amb-70 leads to significant improvement in the selectivity to HMF from glucose. Systems using Sn-β show at least 9% higher selectivity than those using Sn-SBA-15. Using Sn-β/Amb-70 for the conversion of glucose, selectivities of 64, 59 and 70% were obtained, respectively, using GVL, GHL and THF as the solvent.

Monophasic Reactors Using Lactones, Hydrofurans or Hydropyrans with 10% of Water and Heterogeneous Catalysts:

Experimental: In 10 mL thick-walled glass reactors were added 0.03 g of monosaccharide, 0.147 g of water, 1.323 g of organic solvent and the appropriate amount of solid catalyst. The final solution contains 2 wt % of monosaccharide and a weight ratio water:organic solvent of 1:9. The reactor was placed in the oil bath at 403 K and stirred at 700 rpm. Reactors were removed from the oil bath at specific reaction times and cooled in an ice-water bath.

Table 6 shows the results for conversion of fructose and glucose to HMF using Amb-70 or a combination of Amb-70 and Sn-based catalysts (Sn-β or Sn-SBA-15) in GVL, GHL or THF containing 10 wt. % water. These experiments were carried out using different catalysts and solvents at similar conversions (~90%). It can be seen that HMF was obtained from fructose using Amb-70 with selectivities between 80 and 85%. On the other hand, direct dehydration of glucose using Amb-70 led to selectivities lower than 35%, in agreement with early reports showing that direct dehydration of glucose with mineral acids leads to low selectivity to HMF. The combination of a Sn-based catalyst and Amb-70 leads to significant improvement in the selectivity to HMF from glucose. Systems using Sn-β show at least 9% higher selectivity than those using Sn-SBA-15. In this respect, Taarning and co-workers have shown that Sn-β displays higher Lewis acid strength than Sn-SBA-15 which gives it significantly higher catalytic activity. Using Sn-β/Amb-70 for the conversion of glucose, selectivities of 64, 59 and 70% were obtained, respectively, using GVL, GHL and THF as the solvent.

Because methyltetrahydrofuran (MTHF) can be produced directly from biomass-derived furfural or GVL, the use of this solvent was also explored for conversion of glucose to HMF. MTHF is not miscible with water, and the conversion of glucose in a mixture of MTHF and water (9:1 ratio) is biphasic. The selectivity obtained for this system at 90% glucose conversion was 60%, which is comparable to reaction in GHL. To obtain a monophasic solvent system, half of the MTHF was substituted by THF, and the solvent system consisting of THF:MTHF (1:1) and 10 wt. % water produced a selectivity of 66% for HMF formation from glucose, which is comparable to that obtained in GVL.

TABLE 6

Conversion of glucose or fructose to HMF in a monophasic system using γ-lactones, THF or MTHF with water in a ratio (9:1).[a]

| Feed | Solvent | Lewis Acid | Time/min | Conv./% | Selec./% |
|---|---|---|---|---|---|
| Fructose[b] | GVL | — | 9 | 89 | 80 |
| Glucose[c] | GVL | — | 30 | 92 | 32 |
| Glucose[d] | GVL | Sn-β | 20 | 92 | 64 |
| Glucose[e] | GVL | Sn-SBA-15 | 15 | 90 | 51 |
| Fructose[b] | GHL | — | 10 | 91 | 81 |
| Glucose[c] | GHL | — | 30 | 85 | 30 |
| Glucose[d] | GHL | Sn-β | 20 | 93 | 59 |
| Glucose[e] | GHL | Sn-SBA-15 | 15 | 90 | 50 |
| Fructose[b] | THF | — | 10 | 91 | 85 |
| Glucose[c] | THF | — | 50 | 90 | 25 |
| Glucose[d] | THF | Sn-β | 30 | 90 | 70 |
| Glucose[e] | THF | Sn-SBA-15 | 20 | 90 | 40 |
| Glucose[c] | MTHF | — | 70 | 90 | 17 |
| Glucose[d] | MTHF | Sn-β | 50 | 89 | 60 |
| Glucose[c] | MTHF:THF[f] | — | 60 | 85 | 26 |
| Glucose[d] | MTHF:THF[f] | Sn-β | 40 | 91 | 66 |

Figure 15B:
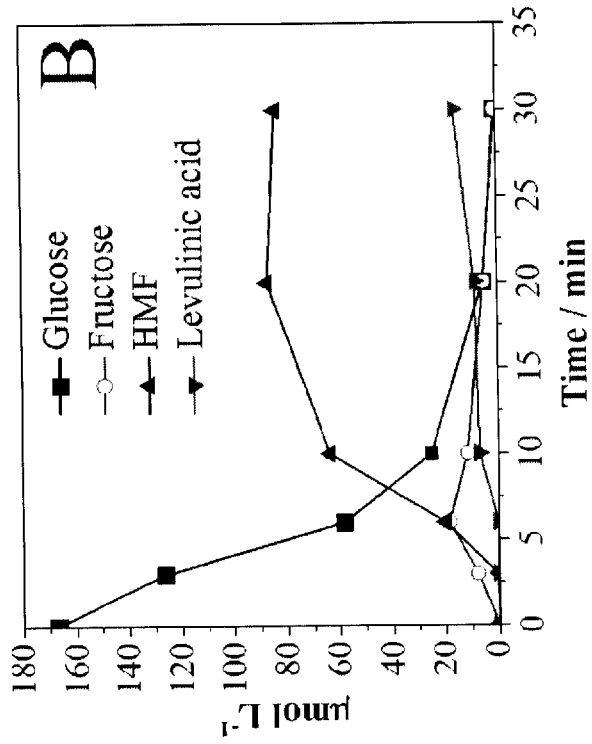
FIGS. 15A, 15B, 15C, 15D, and 15E depict glucose dehydration in various solvents using the disclosed process.
Figure 15A:
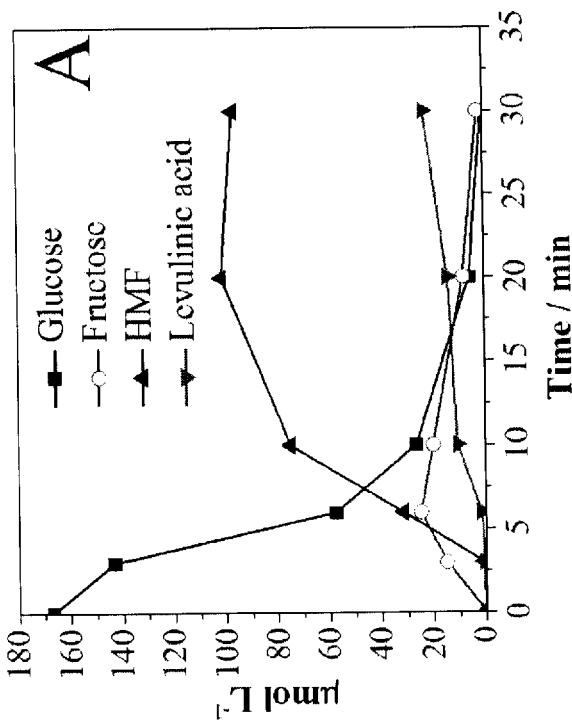
Figure 15D:
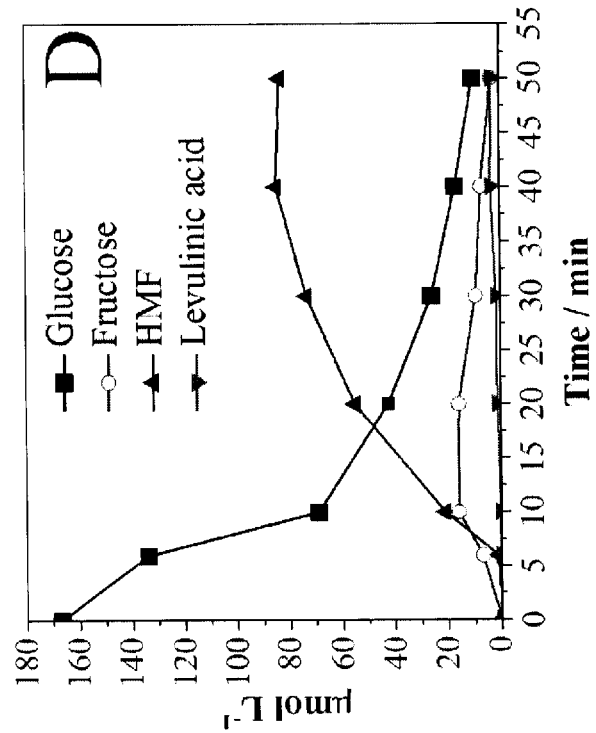
Figure 15C:
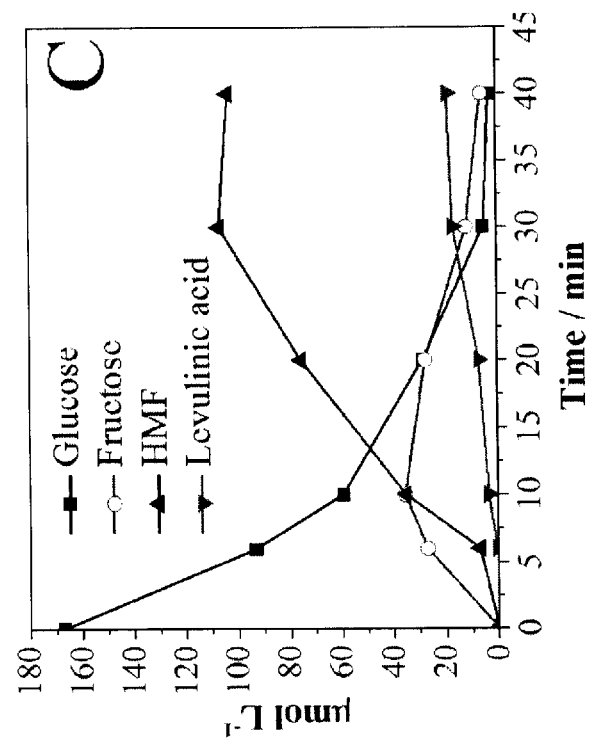
Figure 15E:
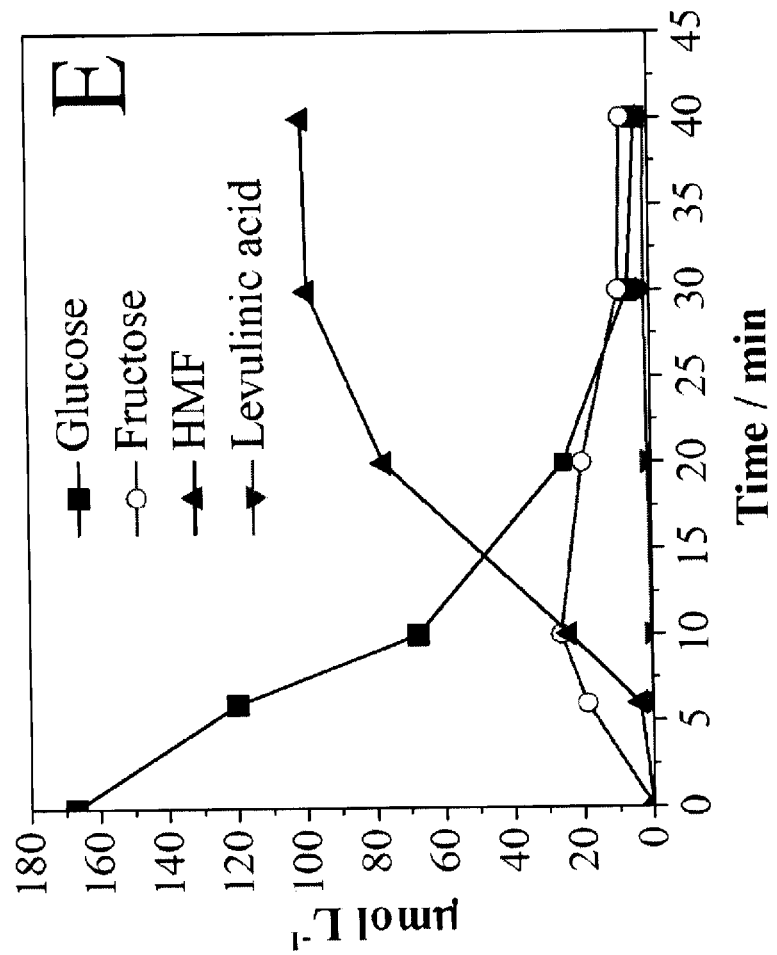

[a]Reaction conditions: 1.5 g of feed (2 wt. % glucose or fructose, organic:water ratio (9:1)); Temperature 130° C.
[b]Catalysts: 0.05 g Amb-70;
[c]Catalysts: 0.1 g Amb-70;
[d]Catalysts: 0.05 g of Sn-β and 0.05 g Amb-70;
[e]Catalysts: 0.05 g of Sn-SBA-15 and 0.05 g Amb-70;
[f]THF:MTHF weight ratio (1:1);

FIGS. 15A to 15E show the conversion of glucose to fructose and HMF as a function of time in the presence of Amb-70 and Sn-β for GVL (FIG. 15A), GHL (FIG. 15B), THF (FIG. 15C), MTHF (FIG. 15D), and THF:MTHF (FIG. 15E). (Each of the stated solvents contained 10 wt % water. For all reactions: 2 wt % glucose; 0.05 g Sn-β; 0.05 g Amb-70; T=130° C.

Figure 16:
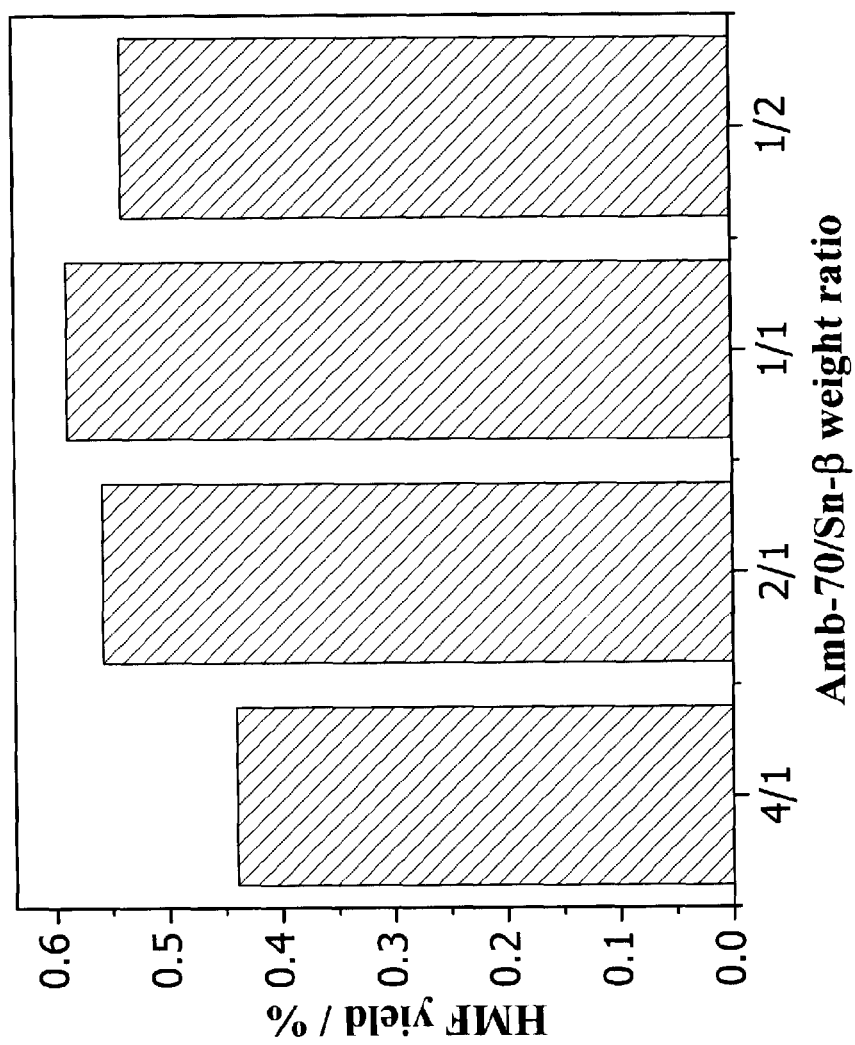
FIG. 16 is a histogram depicting the effect of Amb-70/Sn-β weight ratio on the HMF yield using glucose and GVL:$H_2O$ (9:1) as the solvent.

In glucose conversion (FIGS. 15A-15E), the product observed initially is fructose, and formation of HMF begins at approximately 5 min of reaction time. Comparing the extent of fructose formation in the different solvents, it can be concluded that the effectiveness of glucose isomerization controls the HMF selectivity (see Table 6), i.e., THF>THF: MTHF=GVL>MTHF=GHL. Diminishing the mass ratio Amb-70/Sn-β in an attempt to increase the relative rate of glucose isomerization in GVL did not lead to any improvement in HMF selectivity. The results are shown in FIG. 16, which is a histogram showing % HMF yield as a function of Amb-70/Sn-β weight ratio. Thus, in addition to functioning as a catalyst for glucose isomerization, Sn-β also appears to catalyse fructose degradation to unidentified products. After HMF has been formed, it can undergo further reaction to form equimolar amounts of levulinic (LA) and formic acid (FA), as observed in FIGS. 15A-15E, generated from HMF hydrolysis (HMF=LA+FA). The carbon balances in the reactions carried out using GVL (FIG. 15A), GHL (FIG. 15B) and THF (FIG. 15C) were, respectively, 80, 65 and 85%. Common degradation products, such as humins, formed by the cross-polymerization of glucose and HMF [32] were not quantified.

More Examples of Monophasic Reactors Using Lactones, Hydrofurans or Hydropyrans with 10% of Water and Heterogeneous Catalysts:

TABLE 7

Conversion of glucose or fructose to HMF in a monophasic reactor with using lactones or THF and water in a ratio 9:1.

| Feed | Solvent | Lewis Acid (amount) | Brønsted acids (amount) | Time/min | Conv./% | Selec./% |
|---|---|---|---|---|---|---|
| Fructose | GVL | — | Amberlyst-70 (0.1 g) | 9 | 89 | 75 |
| Glucose | GVL | — | Amberlyst-70 (0.1 g) | 8 | 90 | 28 |
| Glucose | GVL | Sn-SBA-15 (0.05 g) | Amberlyst-70 (0.05 g) | 15 | 90 | 51 |
| Glucose | GVL | SnO$_2$/Al-β (0.05 g) | Amberlyst-70 (0.05 g) | 15 | 89 | 55 |
| Glucose | GVL | Sn-β (0.05 g) | Amberlyst-70 (0.1 g) | 15 | 89 | 62 |
| Glucose | THF | Sn-SBA-15 (0.1 g) | Amberlyst-70 (0.1 g) | 60 | 90 | 40 |
| Fructose | GHL | — | Amberlyst-70 (0.05 g) | 10 | 91 | 81 |
| Glucose | GHL | SnO$_2$/Al-β (0.05 g) | Amberlyst-70 (0.05 g) | 15 | 90 | 50 |
| Fructose | GOL | — | Amberlyst-70 (0.05 g) | 10 | 95 | 64 |
| Glucose | GOL | SnO$_2$/Al-β (0.05 g) | Amberlyst-70 (0.05 g) | 30 | 88 | 39 |

[a]Reaction conditions: 1.5 g of feed (5 wt % cellulose, glucose or fructose, water:organic solvent ratio of 1:9); Temperature 403 K.

GVL and GHL have shown to be the best solvents for the conversion of glucose and fructose to HMF. Using $SnO_2$—Al-β, selectivities around 50% were obtained at approximately 90% glucose conversion.

Comparing different isomerization catalysts for the system using GVL, it was found that, Sn-SBA-15 and $SnO_2$—Al-β have similar results, while Sn-β has a performance slightly superior.

Purifying, Concentrating, Isolating HMF from the Product Mix:

Because HMF is both a final product and a platform chemical to make downstream products, it is important to have efficient methods to separate HMF from the reaction medium or to integrate the production of HMF with subsequent upgrading reactions, thereby decreasing the cost of the final product. GVL and GHL have high boiling points that are similar to HMF; therefore, the separation of HMF from these solvents by distillation requires the use of low pressures and could lead to degradation of HMF. While these issues do not pose technological issues, the do raise economic issues that could impact the profitability of the process. In contrast, THF has a low boiling point (66° C.) and can be easily separated from HMF. In the reaction solvent comprising THF:$H_2O$ in a mass ratio (9:1), THF can be evaporated to yield an aqueous solution of HMF, or alternatively, water can be removed using a drying agent such as magnesium sulfate or calcium chloride, followed by distillation of the THF to obtain pure HMF. Another route to separate HMF from GVL or GHL is to convert HMF to a lower boiling point compound. For example, 2,5-dimethylfuran (DMF) is a fuel additive, [14] and it has a boiling point significantly lower than GVL or GHL. Also, it is more stable than HMF, such that DMF can be removed by distillation. To achieve this separation route, the present inventors have shown (see Examples) that DMF can be produced with 46% yield by hydrogenation of HMF in the presence of lactones using a RuSn/C catalyst at 200° C. See FIGS. 5 and 8. Importantly, this catalyst produced DMF from HMF without conversion of the solvent (GVL or GHL), in accordance with previous literature.[33]

Hydrogenation of HMF in Presence of Lactone:

2,5-Dimethylfuran (DMF) can be produced by hydrogenation of HMF and it can be used as a fuel additive. In a 50 mL Parr reactor 0.5 g of RuSn/C, 20 mL of GVL and 2 wt % HMF were added. After 4 h at 473 K 46% yield of DMF were achieved.

Extraction of HMF from GVL or GHL to Water:

As mentioned above, HMF can be removed from THF by distillation, and it can thus be used directly in the oxidation reaction. Removal of HMF from the less volatile γ-lactones solvents can be achieved by contacting these solutions containing HMF with water and cyclopentane (CP) in different proportions, as shown in Table 8. Similar results can be obtained with methylcyclopentane and any other alkane miscible with the lactones.

TABLE 8

Extraction of HMF from GVL and GHL to water using CP.

| Lactone | Extraction | CP/g | % HMF in water | % Lactone in water. |
|---|---|---|---|---|
| GVL | 1[a] | 20 | 90 | 43 |
|  | 2 | 20 | 80[b] | 5.00 |
|  | 3 | 20 | 97[b] | 1.80 |
|  | 4 | 20 | 99[b] | 0.5 |
| GHL | 1[a] | 16 | 80 | 5.00 |
|  | 2 | 6 | 100[b] | 1.30 |
|  | 3 | 6 | 100[b] | 0.35 |
|  | 2 | 12 | 100[b] | 0.80 |

[a]For the first extraction, one part of a HMF solution in lactone was contacted with one part of water and the amount of CP specified in the table. The aqueous phase was separated from the biphasic mixture for subsequent extractions with CP.

[b]Based on the HMF remained in the aqueous layer on the previous extraction.

Contacting one (1) part of a solution containing HMF in GHL with one (1) part of water and 16 parts of CP, leads to an aqueous layer containing of 80 wt. % of the initial HMF and 5 wt. % of the initial GHL. Contacting the resultant aqueous layer twice with 6 parts of CP decreases the GHL concentration to 0.35 wt. % of the initial value, while retaining all of the HMF in the aqueous layer. The HMF:GHL molar ratio in the final aqueous layer is equal to 2.51. GVL is more soluble in water than GHL; therefore, extraction of HMF from GVL requires several consecutive extractions with CP to yield an aqueous solution with 80 wt. % of the initial HMF amount and 0.5 wt. % of the initial amount of GVL. The HMF:GVL molar ratio in the final aqueous layer is equal to 1.52. The boiling point of CP (50° C.) is much lower than GVL (207° C.) and GHL (219° C.), hence it can be separated easily from the lactone by distillation.

More Examples of Extraction of HMF from GVL or GHL to Water:

In the examples described in Table 9, the catalysts can be separated from the reaction medium by filtration. HMF cannot be separated from the solvents by distillation, due to their high boiling point. An alternative is the extraction of HMF to aqueous layer as described for SBP in ref [6].

The high miscibility of GVL with water makes the extraction of HMF complicated. A mixture of GVL containing 1 wt % of HMF with water was contacted with different solvents in order to selectively remove the GLV from the aqueous layers, maintaining the HMF (Table 9).

TABLE 9

Extraction of HMF to water from GVL

| $H_2O$/g | 1% HMF in GVL/g | Solvent 1 (amount) | Solvent 2 (amount) | HMF/ Aqueous layer | GVL/ Aqueous layer | GVL/HMF (g/g) |
|---|---|---|---|---|---|---|
| 2 | 1 | GUL (1 g) | — | 49% | 29% | 59 |
| 2 | 1 | GUL (1 g) | Hexane (2 g) | 67% | 33% | 48 |
| 2 | 1 | GUL (1 g) | Toluene (2 g) | 44% | 15% | 36 |
| 2 | 1 | GUL (1 g) | Hexane (4 g) | 84% | 35% | 42 |
| 2 | 1 | SBP (1 g) | Hexane (3 g) | 57% | 16% | 28 |

TABLE 9-continued

Extraction of HMF to water from GVL

| $H_2O/g$ | 1% HMF in GVL/g | Solvent 1 (amount) | Solvent 2 (amount) | HMF/ Aqueous layer | GVL/ Aqueous layer | GVL/HMF (g/g) |
|---|---|---|---|---|---|---|
| 2 | 1 | SBP (1 g) | Toluene (3 g) | 38% | 7% | 18 |
| 2 | 1 | SBP (1 g) | Hexane (6 g) | 72% | 18% | 25 |

The best solvent systems to extract HMF from aqueous layer were GUL:hexane (1:4) and SBP/hexane (1:6).
Using GUL:hexane (1:4), 84% of HMF and 35% of GVL were present in the aqueous layer.
Using SBP/hexane (1:6), 72% of HMF and 18% of GVL were present in the aqueous layer.

GHL has a low solubility in water, hence an extraction of HMF to water is similar to that used for SBP in ref [6]. In this case, however, hexane cannot be used, since it is not miscible with GHL. Methylcyclopentane showed a good miscibility with GHL while it does not dissolve HMF. Therefore, GHL containing 1 wt % HMF was contacted with water and methylcyclopentane (Table 10).

TABLE 10

Extraction of HMF to water from GHL

| $H_2O/g$ | 1% HMF in GHL/g | Methylcyclopentane/g | HMF/ Aqueous layer | GHL/ Aqueous layer | GHL/HMF (g/g) |
|---|---|---|---|---|---|
| 2 | 1 | — | 46% | 24% | 50 |
| 2 | 1 | 2 | 63% | 18% | 28 |
| 2 | 1 | 4 | 75% | 18% | 23 |
| 2 | 1 | 8 | 86% | 17% | 19 |
| 2 | 1 | 16 | 88% | 13% | 14 |
| 1 | 1 | 4 | 73% | 9% | 12 |
| 1 | 1 | 8 | 78% | 7% | 9 |

HMF can be extracted from GHL to water when the organic solvent is contacted with methylcyclopentane.
A fraction of GHL was found on the aqueous layer, however in much lower respect to GVL.
In the best condition, the weight ratio GHL/HMF in the aqueous layer is as low as 9, while 25 for GVL/HMF.
Metylcyclopentane has a low boiling point (345 K) and can be easily separated from GHL by distillation.

Production of 2,5-Furandicarboxylic Acid (FDCA):

One of the most attractive compounds that can be produced from HMF is 2,5-furandicarboxylic acid (FDCA). FDCA can be produced by oxidation of HMF with molecular oxygen in an aqueous alkaline solution using, for example, supported gold, platinum or palladium catalysts. [34-36] A great many other oxidation catalysts can also be used. FDCA is a monomer that can be used to produce polymers similar to polyethylene terephthalate (PET). PET has a growing market, with more than 49 million tons produced in 2009.[37] For this reason, FDCA has been rated as a top twelve value added chemical by the U.S. Department of Energy.[38] For the production of FDCA, HMF has to be separated to avoid oxidation of the organic solvent.

Aqueous solutions of HMF and γ-lactones (that could be produced by the method outlined above using CP) were used as feed solutions for studies of HMF oxidation under the reaction conditions proposed by Davis et al.[35] i.e., aqueous solution containing 0.1 mol $L^{-1}$ HMF, 2 mol $L^{-1}$ NaOH, 2000 kPA oxygen, 1 wt. % $Au/TiO_2$ (HMF:Au=100) at 22° C. See FIGS. 11 and 13. Using an aqueous solution of HMF with up to 0.5% of GVL or GHL, yields of 80% for FDCA and 20% for 2-hydroxymethylfurancarboxylic acid (HFCA) were observed, in accordance with previous literature in the absence of lactones. [35] When the reaction was carried out in the presence of larger amounts of lactones (i.e., 5%), yields of 56% for FDCA and 44% for HFCA were observed, and 35% of the γ-lactone was converted to levulinic acid (from GVL) or 4-oxohexanoic acid (from GHL). Separation of FDCA was achieved by decreasing the pH of the reaction mixture to a value of 1, leading to precipitation of FDCA, while HFCA and salt remained in solution. The precipitate was filtered and washed with ethanol.

The overall yields achieved for production of DMF and FDCA on a glucose basis for each of the solvent systems described herein are shown in Reaction Scheme 3:

Reaction Scheme 3

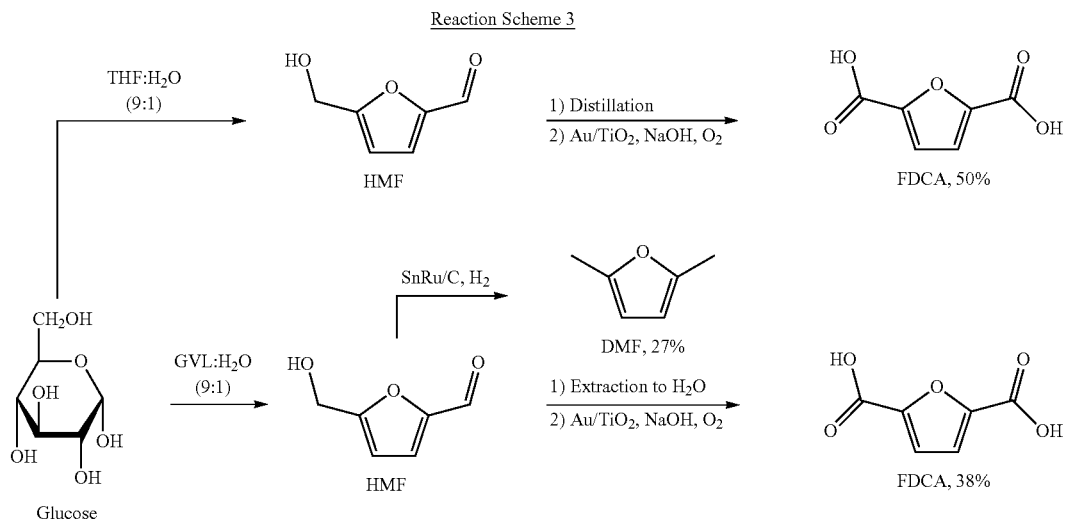

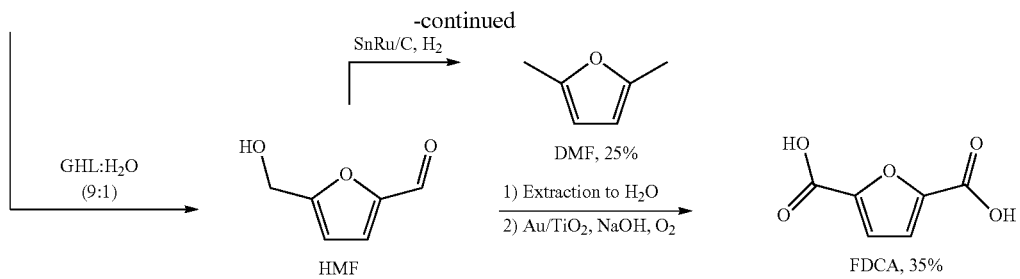

Starting with THF as solvent, an overall yield of 50% is obtained for FDCA, while 38 and 35% are the yields when the process uses GVL and GHL as the solvents, respectively. If the target product is DMF, then yields of 27 and 25% can be obtained in the systems using GVL and GHL as solvents, respectively.

Oxidation of HMF in Presence of Lactones:

HMF can be oxidized into FDCA in presence of the lactones or after being extracted into water using continuous reactor or batch reactors.

Any catalysts able to oxidize HMF can be used in the process. For example, Pt/C and Au/C were placed in a stainless steel tubular reactor (6.35 mm OD) and held between two end plugs of silica granules and quartz wool. The catalyst was reduced in-situ for 3 h at 3000° C. (1° C. min$^{-1}$) before use. The feed was introduced into the reactor using an HPLC pump (Lab Alliance-brand Series I; Scientific System, Inc., State College, Pa., USA). Air or O$_2$ was flow during the reaction (25 cm$^3$(STP)/min) was controlled by a mass flow controller (Brooks Instrument, 5850S; Brooks Instrument, Inc., Hatfield, Pa., USA). The tubular reactor was fitted inside an aluminum block and placed within an insulated furnace (Applied Test Systems, Butler, Pa., USA). Bed temperature was monitored at the reactor wall using a Type K thermocouple (Omega Engineering, Inc., Stamford, Conn., USA) and controlled using a 16A series programmable temperature controller (Love Controls, Inc., Michigan City, Ind., USA). Reactor pressure (1 to 35 bar) was controlled using a back pressure regulator (model BP-60; GO Regulator, Inc, Spartanburg, S.C., USA). The reactor effluent flowed into a vapor-liquid separator wherein the liquid product was collected.

For batch reactions, a 50 mL Parr Instruments Hastelloy C-276 batch reactor (Parr Instrument Company, Moline, Ill., USA), equipped with a variable speed magnetic stirrer, was loaded with reduced and passivated catalyst. The system was purged with helium, pressurized with Air or O$_2$ to the desired pressure and heated to the reaction temperature using a heating mantle. At the end of the reaction, the reactor was cooled and weighed. A sample was taken from the reactor to be analyzed before and at the end of the reaction.

HMF Oxidation in Presence of GVL:

250 mg of 10 wt % Pt/C were loaded in a flow reactor and a solution of 79 wt % GVL, 20 wt % water and 1 wt % HMF. Reaction temperature was set at 100° C. and pressure was set at 13.6 bar of Air.

TABLE 11

Oxidation of FDCA in 4:1 GVL:H$_2$O.[a]

| Feed flow rate (ml/min) | FDCA yield (%) |
|---|---|
| 0.05 | 45 |
| 0.01 | 62 |

[a]100° C., 13.6 bar Air. 250 mg 10 wt % Pt/C

HMF Oxidation in Presence of Water Saturated with GHL:

The feed used is the aqueous layers obtained on the extraction of HMF from GHL to water, as described in Table 12 Reaction was carried out in batch reactor as described in section 4.5.1.

TABLE 12

Oxidation of FDCA in water saturated with GHL.[a]

| Pressure O$_2$ (psia) | Time (h) | T (° C.) | NaOH:HMF ratio | FDCA yield (%) | FMCA yield (%) |
|---|---|---|---|---|---|
| 150 | 4 | 100 | 0 | 4 | 36 |
| 500 | 10 | 100 | 4 | 8 | 36 |
| 500 | 4 | 100 | 20 | 27 | 19 |

[a]0.1 g of 1 wt % Au/ZrO$_2$. 0.5 wt % HMF, 9 wt % GHL lactonce, 90.5 wt % Water Co-Production of HMF and Furfural:

When using biomass as feedstocks, containing C5 and C6 sugars it is possible to produce furfural and HMF at similar conditions. For example using 6.6 wt % of different feedstocks, at 160° C. for 30 min, in 90 wt % GVL/10 wt % water solvent and 0.05 M sulfuric acid as catalyst, yields of 78% furfural and 24% HMF can be obtained from corn cob. Similar numbers can be obtained from other feedstocks as corn stover or sugar cane bagasse.

| Feed | Corn cob | Corn stover | bagasse |
|---|---|---|---|
| Mass (g) | 0.202 | 0.206 | 0.204 |
| Furfural (yield) | 78% | 64% | 91% |
| HMF | 24% | 22% | 23% |

Conclusion:

The highest yields achieved to date for production of HMF from glucose using a combination of Amb-70 and Sn-β as solid acid catalysts are 59, 55 and 63% using GVL, GHL or THF as solvents, respectively. These results are comparable or higher than values obtained in the literature using a combination of Lewis and Brønsted acids. In addition to achieving high yields, the systems disclosed herein can replace the use of homogeneous catalysts and salts, leading to a more sustainable and economically viable process. Separation and purification of HMF can be achieved by distillation for the case of THF as the solvent. In contrast, GVL and GHL have boiling points that are similar to HMF, requiring the isolation of HMF by different methods. For example, HMF can be converted to DMF with 46% yield, and this low boiling point product can then be separated from the solvent by distillation. Alternatively, HMF can be extracted to water assisted by hydrocarbons such as cyclopentane. The oxidation of HMF to FDCA can then be carried out in the presence of small amounts of lactones, and yields of 80% were obtained. Thus, the catalytic systems described herein can not only replace the use of homogeneous catalysts and salts, but they also allow the integration of HMF production with processes for HMF upgrading to value-added downstream products.

Monophasic Reactors Using Lactones, Hydrofurans or Hydropyranswith 10 Wt. % Water and Homogeneous Catalysts:

In 10 mL thick-walled glass reactors, 0.294 g of a 25 mM $AlCl_3$ aqueous solution with pH adjusted to 1.8 with HCl, 1.176 g of organic solvents and 0.03 g of cellulose or monosaccharide were added to the reactor. The final concentrations were 2 wt. % of cellulose or monosaccharide, 5 mmol $L^{-1}$ of $AlCl_3$ and 3.2 mmol $L^{-1}$ of HCl. The reactor was placed in an oil bath at 170° C. and stirred at 700 rpm. Reactors were removed from the oil bath at specific reaction times and cooled in an ice-water bath.

Monophasic Reactors Using Lactones, Hydrofurans and Judropyranswith 10 Wt. % Water and Heterogeneous Catalysts:

In 10 mL thick-walled glass reactors, 0.03 g of monosaccharide, 0.147 g of water, 1.323 g of organic solvent and the appropriate amount of solid catalyst were added to the reactor. The final solution contained 2 wt. % of monosaccharide and a weight ratio organic:water solvent of (9:1). The reactor was placed in the oil bath at 130° C. and stirred at 700 rpm. Reactors were removed from the oil bath at specific reaction times and cooled in an ice-water bath.

Hydrogenolysis of HMF in Presence of Lactone:

In a 50 mL Parr reactor, 0.5 g of SnRu/C, 20 mL of GVL and 2 wt % HMF were added. The reaction was carried out at 200° C. for 4 h.

Oxidation of HMF in Presence of Lactones:

HMF was oxidized in a 50 mL Parr reactor. An aqueous solution containing 0.1 mol $L^{-1}$ HMF and 2 mol $L^{-1}$ NaOH was reacted at 22° C. for 22 h under 2000 kPA of oxygen using 1 wt % $Au/TiO_2$ (HMF:Au=100). To study the effect of γ-lactones on the HMF oxidation, different γ-lactones were added to the aqueous solution.

References Cited

The following documents are incorporated herein by reference.

1. J. J. Bozell and G. R. Petersen, *Green Chemistry*, 2010, 12, 539-554.
2. M. J. Antal Jr, W. S. L. Mok and G. N. Richards, *Carbohydrate Research*, 1990, 199, 91-109.
3. J. Guan, Q. A. Cao, X. C. Guo and X. D. Mu, *Comput Theor Chem*, 2011, 963, 453-462.
4. A. S. Amarasekara, L. D. Williams and C. C. Ebede, *Carbohydrate Research*, 2008, 343, 3021-3024.
5. J. F. Robyt, *Essentials of carbohydrate chemistry*, Springer Pub. Co., New York, 1998.
6. Y. J. Pagan-Torres, T. F. Wang, J. M. R. Gallo, B. H. Shanks and J. A. Dumesic, *Acs Catal*, 2012, 2, 930-934.
7. C. Moreau, A. Finiels and L. Vanoye, *Journal of Molecular Catalysis A: Chemical*, 2006, 253, 165-169.
8. Y. Roman-Leshkov, J. N. Chheda and J. A. Dumesic, *Science*, 2006, 312, 1933-1937.
9. J. N. Chheda, Y. Roman-Leshkov and J. A. Dumesic, *Green Chemistry*, 2007, 9, 342-350.
10. A. J. Crisci, M. H. Tucker, M. Y. Lee, S. G. Jang, J. A. Dumesic and S. L. Scott, *Acs Catal*, 2011, 1, 719-728.
11. H. Zhao, J. E. Holladay, H. Brown and Z. C. Zhang, *Science*, 2007, 316, 1597-1600.
12. J. B. Binder and R. T. Raines, *Journal of the American Chemical Society*, 2009, 131, 1979-1985.
13. G. Yong, Y. Zhang and J. Y. Ying, *Angewandte Chemie International Edition*, 2008, 47, 9345-9348.
14. Y. Roman-Leshkov, C. J. Barrett, Z. Y. Liu and J. A. Dumesic, *Nature*, 2007, 447, 982-U985.
15. Y. Roman-Leshkov and J. Dumesic, *Topics in Catalysis*, 2009, 52, 297-303.
16. K.-i. Shimizu, R. Uozumi and A. Satsuma, *Catalysis Communications*, 2009, 10, 1849-1853.
17. Y. Zhang, K. Hidajat and A. K. Ray, *Biochemical Engineering Journal*, 2004, 21, 111-121.
18. H. B. Zhao, J. E. Holladay, H. Brown and Z. C. Zhang, *Science*, 2007, 316, 1597-1600.
19. M. E. Zakrzewska, E. Bogel-Lukasik and R. Bogel-Lukasik, *Chem Rev*, 2011, 111, 397-417.
20. R. L. Huang, W. Qi, R. X. Su and Z. M. He, *Chem Commun*, 2010, 46, 1115-1117.
21. D. M. Alonso, J. Q. Bond and J. A. Dumesic, *Green Chemistry*, 2010, 12, 1493-1513.
22. J. C. Serrano-Ruiz, R. Luque and A. Sepulveda-Escribano, *Chem Soc Rev*, 2011, 40, 5266-5281.
23. L. E. Manzer, *Appl Catal a-Gen*, 2004, 272, 249-256.
24. T. M. Ugurchieva, A. V. Lozanova, M. V. Zlokazov and V. V. Veselovsky, *Russ Chem B+*, 2008, 57, 657-659.
25. Y. Zhou, L. K. Woo and R. J. Angelici, *Applied Catalysis A: General*, 2007, 333, 238-244.
26. O. W. Cass, *Industrial & Engineering Chemistry*, 1948, 40, 216-219.
27. E. J. Garcia-Suarez, A. M. Balu, M. Tristany, A. B. Garcia, K. Philippot and R. Luque, *Green Chemistry*, 2012, 14, 1434-1439.
28. A. Takagaki, M. Ohara, S, Nishimura and K. Ebitani, *Chem Commun*, 2009, 6276-6278.
29. M. Moliner, Y. Roman-Leshkov and M. E. Davis, *P Natl Acad Sci USA*, 2010, 107, 6164-6168.
30. E. Nikolla, Y. Roman-Leshkov, M. Moliner and M. E. Davis, *Acs Catal*, 2011, 1, 408-410.
31. C. M. Osmundsen, M. S. Holm, S. Dahl and E. Taarning, *P Roy Soc a-Math Phy*, 2012, 468, 2000-2016.
32. H. M. Pilath, M. R. Nimlos, A. Mittal, M. E. Himmel and D. K. Johnson, *J Agr Food Chem*, 2010, 58, 6131-6140.
33. S. G. Wettstein, D. M. Alonso, Y. Chong and J. A. Dumesic, *Energy & Environmental Science*, 2012, 5, 8199-8203.
34. B. N. Zope, S. E. Davis and R. J. Davis, *Topics in Catalysis*, 2012, 55, 24-32.
35. S. E. Davis, B. N. Zope and R. J. Davis, *Green Chemistry*, 2012, 14, 143-147.
36. S. E. Davis, L. R. Houk, E. C. Tamargo, A. K. Datye and R. J. Davis, *Catal Today*, 2011, 160, 55-60.
37. In *Eurasian Chemical Market Inetrnational Magazine*, 2011, vol. 8, p. 56.
38. T. A. Werpy and G. Petersen, U.S. Department of Energy, 2004.
39. P. Shah, A. V. Ramaswamy, K. Lazar and V. Ramaswamy, *Micropor Mesopor Mat*, 2007, 100, 210-226.
40. Wyman, C. E., et al., *Coordinated development of leading biomass pretreatment technologies*. Bioresource Technology, 2005. 96(18): p. 1959-1966.
41. Alamillo, R., et al., *The selective hydrogenation of biomass-derived 5-hydroxymethylfurfural using heterogeneous catalysts*. Green Chemistry, 2012. 14(5): p. 1413-1419.
42. Tucker, M. H., *Selective Production of Value Added Chemicals From Fructose Using Heterogeneous Catalysis*, in Chemical & Biological Engineering. 2011, University of Wisconsin-Madison: Madison.

43. Dutta, S., et al., *Direct conversion of cellulose and lignocellulosic biomass into chemicals and biofuel with metal chloride catalysts.* Journal of Catalysis, 2012. 288: p. 8-15.
44. Yang, Y., C. W. Hu, and M. M. Abu-Omar, *Conversion of carbohydrates and lignocellulosic biomass into 5-hydroxymethylfurfural using AlCl3 center dot 6H(2)O catalyst in a biphasic solvent system.* Green Chemistry, 2012. 14(2): p. 509-513.

What is claimed is:

1. A process to produce 5-hydroxymethylfurfural (HMF), the process comprising:
reacting a C6 sugar-containing reactant in a monophasic reaction solution comprising (i) an organic solvent selected from the group consisting of beta-, gamma-, and delta-lactones, hydrofurans, hydropyrans, and combinations thereof, and (ii) at least about 1 wt % water; in the presence of a heterogenous acid catalyst for a time and under conditions wherein at least a portion of the C6 sugar present in the reactant is converted to HMF.

2. The method of claim 1, wherein the organic solvent is miscible with water.

3. The method of claim 1, wherein the organic solvent can dissolve from 2 wt % to 25 wt % water.

4. The method of claim 1, wherein the organic solvent is a combination of two or more solvents, wherein at least one of the solvents is miscible with water and at least one of the other solvents is not miscible with water.

5. The method claim 1, further comprising subjecting the HMF to a hydrogenolysis reaction in the presence of a suitable catalyst, for a time and under conditions wherein at least a portion of the HMF is converted to dimethylfuran.

6. The method claim 1, further comprising oxygenating the HMF in the presence of an oxygenation catalyst, for a time and under conditions wherein at least a portion of the HMF is converted to furandicarboxylic acid.

7. The method of claim 1, wherein the heterogeneous acid catalyst is a solid acid catalyst selected from the group consisting of solid Brønsted acid catalysts, solid Lewis acid catalysts, and combinations thereof.

8. The method of claim 7, wherein the solid acid catalyst is a heteropolyacid.

9. The method of claim 7, wherein the solid acid catalyst is a mesoporous silica.

10. The method of claim 7, wherein the solid acid catalyst is a zeolite.

11. The method of claim 7, wherein the solid acid catalyst is an acidic material on a thermo-stable support.

12. The method of claim 11, wherein the thermostable support is selected from the group consisting of tin oxide, alumina, niobia, zirconia, titania, and carbon.

13. The method of claim 7, wherein the solid acid catalyst is a solid acidic metal oxide.

14. The method of claim 7, wherein the solid acid catalyst is a solid acidic ion exchanger.

15. The method of claim 14, wherein the acidic ion exchanger comprises cross-linked polystyrene-containing sulfonic acid groups.

16. The method of claim 14, wherein the acidic ion exchanger comprises sulfonated tetrafluoroethylene-based fluoropolymer-copolymers.

17. The method claim 7, further comprising subjecting the HMF to a hydrogenolysis reaction in the presence of a suitable catalyst for a time and under conditions wherein at least a portion of the HMF is converted to dimethylfuran.

18. The method claim 7, further comprising oxygenating the HMF in the presence of an oxygenation catalyst, for a time and under conditions wherein at least a portion of the HMF is converted to furandicarboxylic acid.

19. The method of claim 1, wherein the monophasic reaction solution comprises from about 5 wt % to about 20 wt % water.

20. The method of claim 1, wherein the monophasic reaction solution comprises from about 5 wt % to about 12 wt % water.

21. The method of claim 1, further comprising, after reacting the C6 sugar-containing reactant to yield HMF, adding a sufficient quantity of a mixture of water and hydrocarbon to the monophasic reaction solution to create a biphasic system having an organic phase and an aqueous phase, wherein at least a portion of the HMF is extracted into the resulting aqueous phase.

22. The method claim 21, further comprising subjecting the HMF to a hydrogenolysis reaction in the presence of a suitable catalyst for a time and under conditions wherein at least a portion of the HMF is converted to dimethylfuran.

23. The method claim 21, further comprising oxygenating the HMF in the presence of an oxygenation catalyst, for a time and under conditions wherein at least a portion of the HMF is converted to furandicarboxylic acid.

24. A process to produce 5-hydroxymethylfurfural (HMF), the process comprising:
reacting a C6 sugar-containing reactant in a biphasic reaction solution comprising (i) an aqueous phase, and (ii) an organic phase comprising a water-immiscible solvent selected from the group consisting of beta-, gamma-, and delta-lactones, hydrofurans, hydropyrans, and combinations thereof; in the presence of an acid catalyst for a time and under conditions wherein at least a portion of the C6 sugar present in the reactant is converted to HMF.

25. The method of claim 24, wherein the aqueous phase comprises a saturating amount of a salt.

26. The method of claim 24, wherein the acid catalyst is selected from the group consisting of Brønsted acid catalysts, Lewis acid catalysts, and combinations thereof.

27. The method of claim 24, wherein the organic solvent has from five (5) carbon atoms to sixteen (16) carbon atoms.

28. The method of claim 24, wherein the organic solvent has from five (5) carbon atoms to eleven (11) carbon atoms.

29. The method claim 24, further comprising subjecting the HMF to a hydrogenolysis reaction in the presence of a suitable catalyst for a time and under conditions wherein at least a portion of the HMF is converted to dimethylfuran.

30. The method claim 24, further comprising oxygenating the HMF in the presence of an oxygenation catalyst, for a time and under conditions wherein at least a portion of the HMF is converted to furandicarboxylic acid.

* * * * *